United States Patent
Kao et al.

(10) Patent No.: US 10,130,430 B2
(45) Date of Patent: Nov. 20, 2018

(54) NO-TOUCH SURGICAL NAVIGATION METHOD AND SYSTEM THEREOF

(71) Applicant: INTAI TECHNOLOGY CORP., Taichung (TW)

(72) Inventors: Kuo-Tung Kao, Taichung (TW); Chen-Tai Lin, Taichung (TW); Ying-Yi Cheng, Taichung (TW); Shih-Chang Chuang, Taichung (TW); Chih-Yen Chiang, Taichung (TW)

(73) Assignee: INTAI TECHNOLOGY CORP., Taichung (TW)

( * ) Notice: Subject to any disclaimer, the term of this patent is extended or adjusted under 35 U.S.C. 154(b) by 0 days.

(21) Appl. No.: 15/784,181

(22) Filed: Oct. 15, 2017

(65) Prior Publication Data

US 2018/0132946 A1 May 17, 2018

Related U.S. Application Data

(60) Provisional application No. 62/421,995, filed on Nov. 14, 2016.

(30) Foreign Application Priority Data

Jul. 28, 2017 (CN) .......................... 2017 1 0630485

(51) Int. Cl.
*G06K 9/00* (2006.01)
*A61B 34/20* (2016.01)
(Continued)

(52) U.S. Cl.
CPC ............ *A61B 34/20* (2016.02); *G06K 9/6201* (2013.01); *G06T 7/0014* (2013.01); *G06T 7/248* (2017.01);
(Continued)

(58) Field of Classification Search
CPC ............ A61B 34/20; A61B 2034/2055; A61B 2034/2061; A61B 2034/2065; G06T 7/80;
(Continued)

(56) References Cited

U.S. PATENT DOCUMENTS 6,505,065 B1 * 1/2003 Yanof ..................... A61N 5/103
600/103
7,840,256 B2 11/2010 Lakin et al.
(Continued)

FOREIGN PATENT DOCUMENTS

CA 2982518 A1 10/2016
CA 2985061 A1 11/2016
(Continued)

*Primary Examiner* — Shefali D Goradia
(74) *Attorney, Agent, or Firm* — CKC & Partners Co., Ltd.

(57) ABSTRACT

A no-touch surgical navigation method for guiding a surgical instrument corresponding to a part of a patient's anatomy is provided. An image registration step is for matching the preoperative implant device planning image and the part of the patient's anatomy via a spatial coordinate transformation relationship. An instrument checking step is for identifying the surgical instrument, and then calibrating a size of the surgical instrument to display an instrument tip mark on the displaying device. An implant device placement selecting step is for moving the surgical instrument by a user, and then the instrument tip mark is synchronously moved with the surgical instrument to select a virtual surgical instrument pattern. A skin incision and trajectory guiding step is for moving the surgical instrument according to a skin incision and trajectory guiding picture so as to move the instrument tip mark close to a planned surgical position.

26 Claims, 17 Drawing Sheets

(51) Int. Cl.
　　　*G06T 7/246* (2017.01)
　　　*G06T 7/33* (2017.01)
　　　*G06T 7/80* (2017.01)
　　　*G06K 9/62* (2006.01)
　　　*G06T 7/00* (2017.01)
　　　*G06T 11/00* (2006.01)

(52) U.S. Cl.
　　　CPC ............... *G06T 7/337* (2017.01); *G06T 7/80* (2017.01); *G06T 11/003* (2013.01); *A61B 2034/2055* (2016.02); *A61B 2034/2061* (2016.02); *A61B 2034/2065* (2016.02); *G06K 2209/057* (2013.01); *G06T 11/001* (2013.01); *G06T 2207/10116* (2013.01); *G06T 2207/30052* (2013.01); *G06T 2207/30088* (2013.01); *G06T 2207/30241* (2013.01)

(58) Field of Classification Search
　　　CPC ....... G06T 7/337; G06T 7/248; G06T 7/0014; G06T 11/003; G06T 11/001; G06T 2207/10116; G06T 2207/30052; G06T 2207/30088; G06T 2207/30241; G06K 9/6201; G06K 2209/057
　　　See application file for complete search history.

(56) References Cited

U.S. PATENT DOCUMENTS

| | | | |
|---|---|---|---|
| 8,214,014 | B2 | 7/2012 | Pacheco |
| 8,842,893 | B2 | 9/2014 | Teichman et al. |
| 9,107,723 | B2* | 8/2015 | Hall .................. A61C 13/0004 |
| 9,326,830 | B2* | 5/2016 | Kitching ................ A61C 7/002 |
| 9,980,780 | B2* | 5/2018 | Lang .................. A61B 34/74 |
| 10,070,903 | B2* | 9/2018 | Blau .................... A61B 17/744 |
| 2008/0200794 | A1 | 8/2008 | Teichman |
| 2011/0046636 | A1* | 2/2011 | Wu ........................ A61B 90/39 |
| | | | 606/130 |
| 2014/0081128 | A1 | 3/2014 | Verard et al. |
| 2016/0310042 | A1 | 10/2016 | Kesten et al. |
| 2017/0116729 | A1 | 4/2017 | Stolka et al. |

FOREIGN PATENT DOCUMENTS

| | | |
|---|---|---|
| TW | 558689 B | 10/2003 |
| WO | 2013119801 A3 | 6/2015 |

* cited by examiner

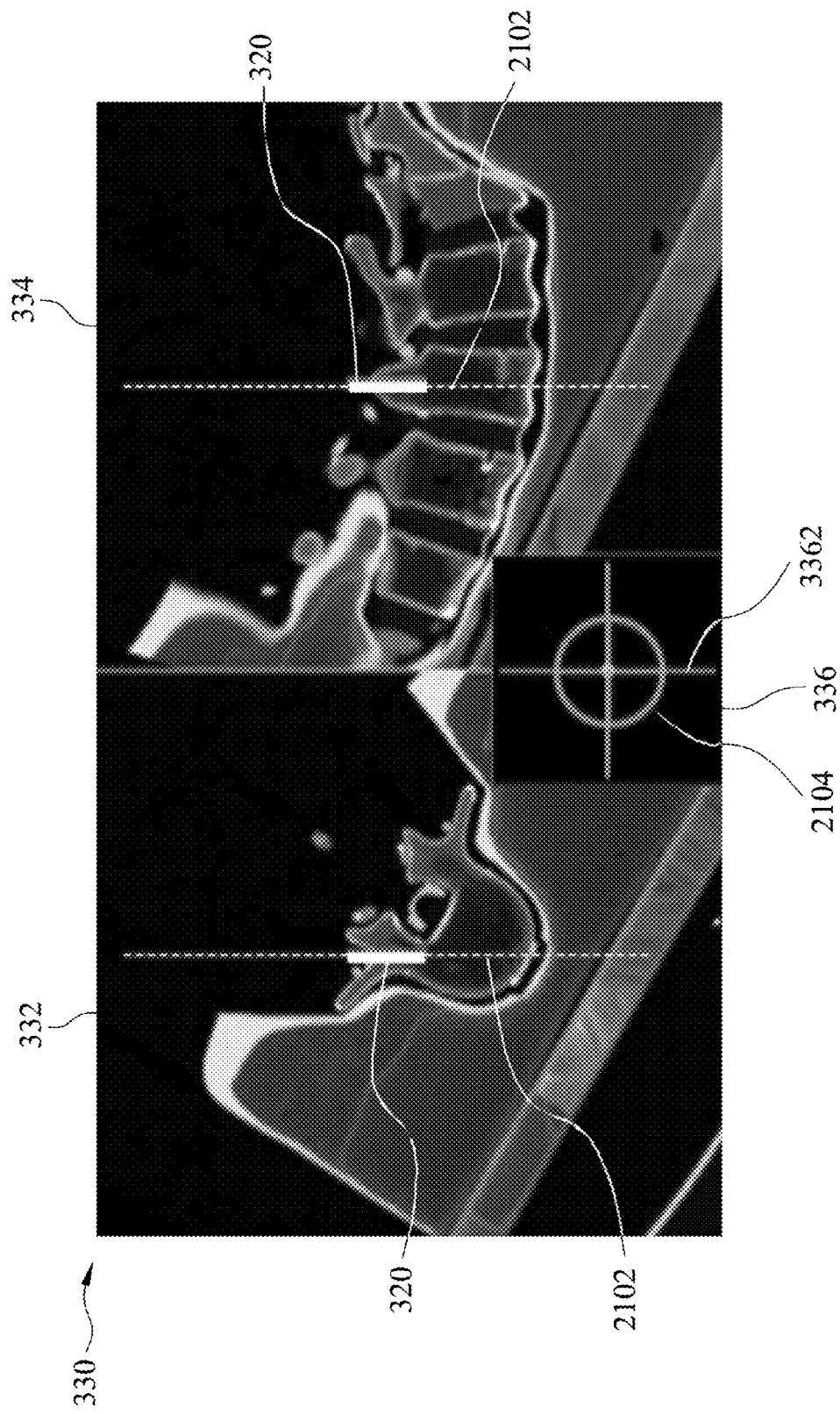

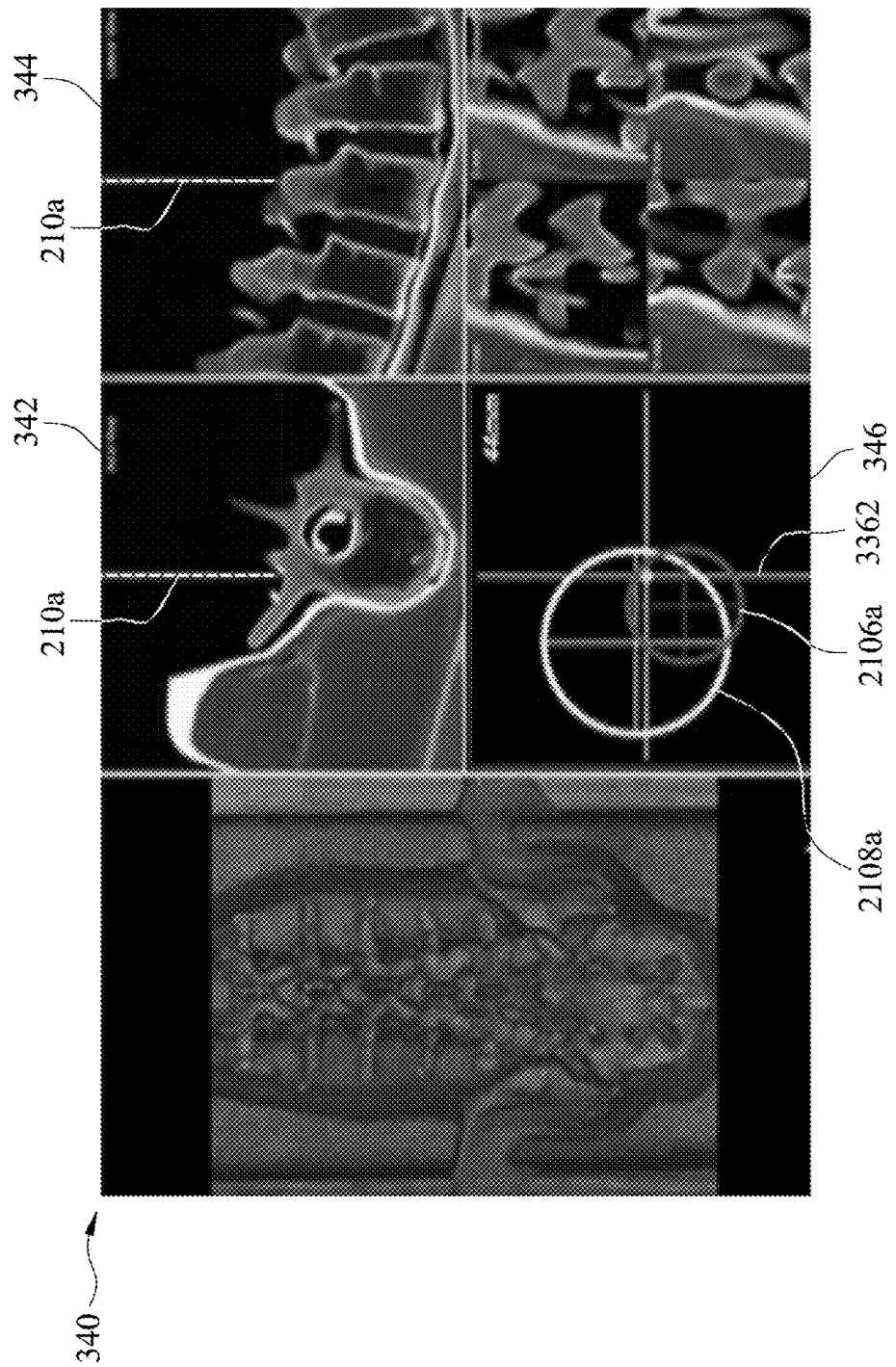

340

Instrument type
◉ Guiding probe
○ Screw Diver
○ Awl
○ Tap
○ Trail

☑ Automatic correction

Select diameter
○ 2.0 mm  ○ 5.0 mm   ○ 8.0 mm
○ 2.5 mm  ○ 5.5 mm   ○ 8.5 mm
○ 3.0 mm  ○ 6.0 mm   ○ 9.0 mm
○ 3.2 mm  ○ 6.7 mm   ○ 10.0 mm
○ 4.0 mm  ○ 7.0 mm   ○ 10.5 mm
○ 4.5 mm  ○ 7.5 mm Remove instrument        Clear all Screw length
○ 25 mm
○ 30 mm
○ 35 mm
○ 40 mm
○ 45 mm
○ 50 mm

Fig. 6D

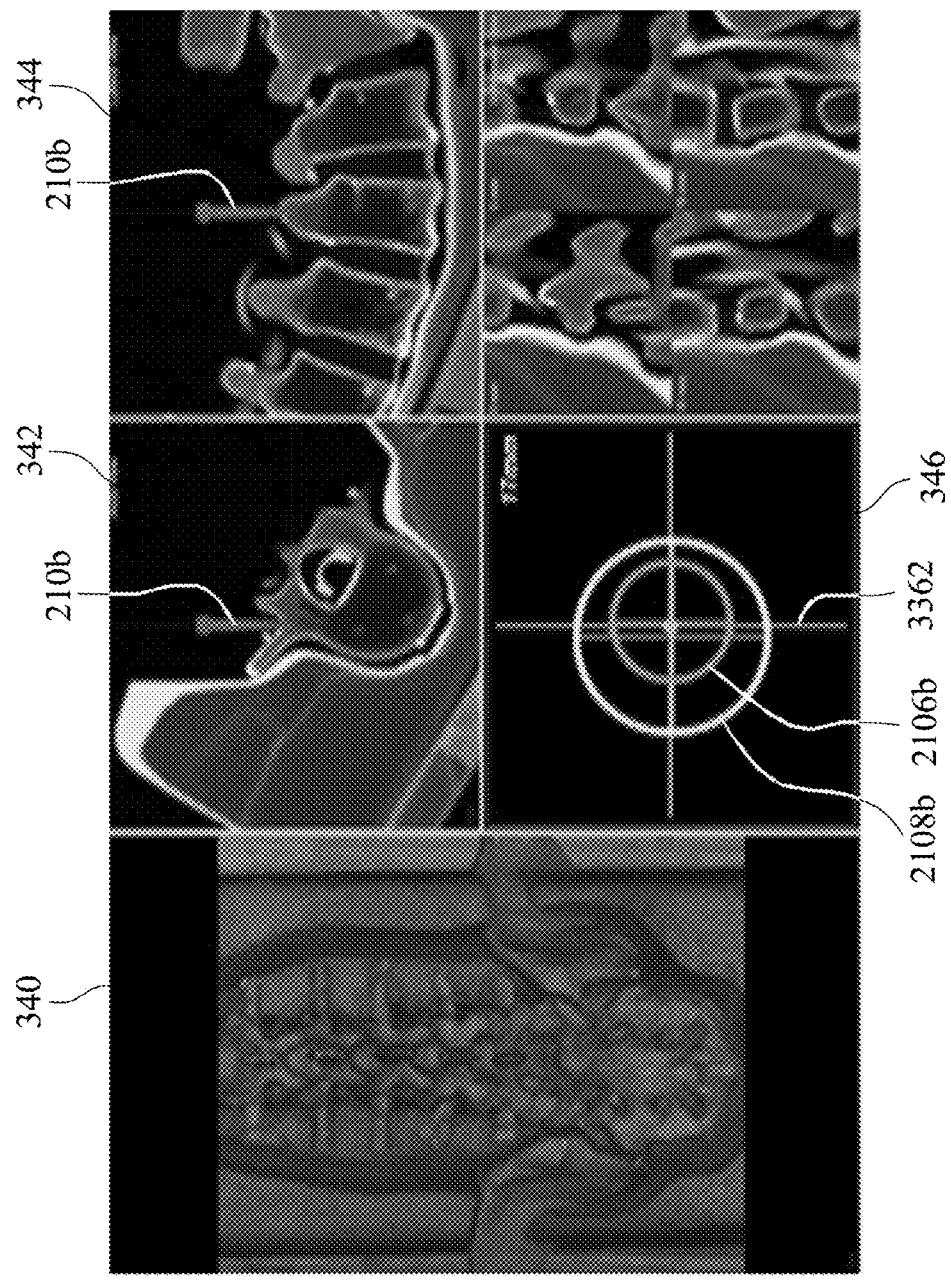

NO-TOUCH SURGICAL NAVIGATION METHOD AND SYSTEM THEREOF

RELATED APPLICATIONS

This application claims priority to U.S. Provisional Application Ser. No. 62/421,995 filed Nov. 14, 2016, and China application No. 201710630485.6 filed on Jul. 28, 2017, the disclosures of which are incorporated herein by reference in their entireties.

BACKGROUND

Technical Field

The present disclosure relates to a surgical navigation method and a surgical navigation system thereof. More particularly, the present disclosure relates to a no-touch surgical navigation method and a no-touch surgical navigation system thereof.

Description of Related Art

Surgical navigation systems, also known as computer assisted surgery and image guided surgery, aid surgeons (i.e., physicians) in locating patient anatomical structures, guiding surgical instruments (such as a bone screw), and implanting medical devices with a high degree of accuracy. A conventional surgical navigation system typically includes a processing unit, a tracking device, and patient anatomical information. The patient anatomical information can be obtained by using a 2D/3D imaging mode such a fluoroscopy, computer tomography (CT), a C-arm X-ray machine or by simply defining the location of patient anatomy with the surgical navigation system. Surgical navigation systems can be used for a wide variety of surgeries to improve patient outcomes.

Conventional surgical navigation systems generally include a touch screen for selecting information and controlling surgical operations via an operator action. In one surgical procedure, the physician needs to alternatively operate surgical instruments and the conventional surgical navigation system. In another surgical procedure, the physician and the operator operate surgical instruments and the conventional surgical navigation system, respectively. No matter what procedure is employed, the conventional surgical navigation system requires an additional human support to control redundant touch and increases surgical procedural complexity, thereby increasing failure risk caused by a human error. In particular, when the surgical instrument is replaced, the accuracy, reliability and safety of the system will be significantly decreased. Therefore, a surgical navigation system and a surgical navigation method having the features of no redundant touch, high safety, high accuracy, high precision and convenient operation are commercially desirable. A no-touch surgical navigation system and a no-touch surgical navigation method of the present disclosure are proposed to overcome the conventional problems.

SUMMARY

According to one aspect of the present disclosure, a no-touch surgical navigation method for guiding a surgical instrument corresponding to a part of a patient's anatomy provides a preoperative implant device planning step, an image registration step, an instrument checking step, an implant device placement selecting step and a skin incision and trajectory guiding step. The preoperative implant device planning step is for acquiring at least one preoperative implant device planning image and visualizing the preoperative implant device planning image on a displaying device. The image registration step is for establishing a spatial coordinate transformation relationship between the part of the patient's anatomy and the preoperative implant device planning image, and matching the preoperative implant device planning image and the part of the patient's anatomy via the spatial coordinate transformation relationship. The instrument checking step is for identifying the surgical instrument, and then calibrating a size of the surgical instrument to display an instrument tip mark of the surgical instrument on the displaying device. The implant device placement selecting step is for moving the surgical instrument by a user, and the instrument tip mark is synchronously moved with the surgical instrument to select a virtual surgical instrument pattern in the preoperative implant device planning image, and then a skin incision and trajectory guiding picture is shown on the displaying device. The skin incision and trajectory guiding step is for moving the surgical instrument by the user according to the skin incision and trajectory guiding picture so as to move the instrument tip mark close to a planned surgical position, and the planned surgical position is displayed in the skin incision and trajectory guiding picture.

According to another aspect of the present disclosure, a no-touch surgical navigation method for guiding a plurality of surgical instruments corresponding to a part of the patient's anatomy provides a preoperative implant device planning step, an image registration step, a first instrument checking step, an implant device placement selecting step, a skin incision and trajectory guiding step, an instrument replacing step, a second instrument checking step and a surgical instrument trajectory guiding step. The surgical instruments include a first surgical instrument and a second surgical instrument. The preoperative implant device planning step is for acquiring at least one preoperative implant device planning image and visualizing the preoperative implant device planning image on a displaying device. The image registration step is for establishing a spatial coordinate transformation relationship between the part of the patient's anatomy and the preoperative implant device planning image, and matching the preoperative implant device planning image and the part of the patient's anatomy via the spatial coordinate transformation relationship. The first instrument checking step is for identifying the first surgical instrument, and then calibrating a size of the first surgical instrument to display a first instrument tip mark of the first surgical instrument on the displaying device. The implant device placement selecting step is for moving the first surgical instrument by a user, and the first instrument tip mark is synchronously moved with the first surgical instrument to select a virtual second surgical instrument pattern in the preoperative implant device planning image. Then, a skin incision and trajectory guiding picture is shown on the displaying device. The skin incision and trajectory guiding step is for moving the first surgical instrument by the user according to the skin incision and trajectory guiding picture so as to move the first instrument tip mark close to a planned surgical position. The planned surgical position is displayed in the skin incision and trajectory guiding picture. When the first instrument tip mark is aligned with the planned surgical position, the skin incision and trajectory guiding picture is changed to a surgical instrument guiding picture on the displaying device. The instrument replacing step is for replacing the first surgical instrument with the second surgical instrument by the user. The second instrument checking step is for identifying the second surgical instrument, and then calibrating a size of the second surgical instrument to display a second instrument tip mark of the second surgical instrument on the displaying device. The surgical instrument trajectory guiding step is for moving the second surgical instrument close to the planned surgical position according to the surgical instrument guiding picture.

According to further another aspect of the present disclosure, a no-touch surgical navigation system using the no-touch surgical navigation method includes a surgical instrument, a displaying device, an optical tracker and a processing unit. The surgical instrument moved by the user and connected to an instrument optical sensing device. The displaying device includes a screen which displays a preoperative implant device planning image, a skin incision and trajectory guiding picture or a surgical instrument guiding picture. The optical tracker is configured to sense the instrument optical sensing device. The instrument optical sensing device is oriented towards the optical tracker so as to identify the surgical instrument by the optical tracker and obtain a surgical instrument datum corresponding to the surgical instrument. The processing unit is signally connected to the displaying device and the optical tracker. The processing unit includes a preoperative implant device planning module, an image registration module, an instrument checking module, an implant device placement selecting module and a trajectory guiding module. The preoperative implant device planning module is configured to acquire the preoperative implant device planning image and visualize the preoperative implant device planning image on the screen. The image registration module is signally connected to the preoperative implant device planning module. The image registration module is configured to establish the spatial coordinate transformation relationship between the part of the patient's anatomy and the preoperative implant device planning image, and match the preoperative implant device planning image and the part of the patient's anatomy via the spatial coordinate transformation relationship. The instrument checking module is signally connected to the image registration module and the screen. The instrument checking module is configured to receive the surgical instrument datum and identify a position of the surgical instrument on the screen, and then calibrate the size of the surgical instrument to display the instrument tip mark of the surgical instrument on the screen. The implant device placement selecting module is signally connected to the instrument checking module and the image registration module. The implant device placement selecting module is configured to select a virtual surgical instrument pattern in the preoperative implant device planning image by moving the instrument tip mark of the surgical instrument so as to display the skin incision and trajectory guiding picture on the screen. The trajectory guiding module is signally connected to the instrument checking module and the implant device placement selecting module. The trajectory guiding module is configured to move the instrument tip mark close to a planned surgical position by moving the surgical instrument according to the skin incision and trajectory guiding picture on the screen.

BRIEF DESCRIPTION OF THE DRAWINGS

The present disclosure can be more fully understood by reading the following detailed description of the embodiment, with reference made to the accompanying drawings as follows:

FIG. 3B shows a schematic view of a skin incision and trajectory guiding picture on the displaying device according to the first embodiment of the present disclosure;

FIG. 6C shows a schematic view of a surgical instrument guiding picture on the displaying device for guiding the first surgical instrument according to the second embodiment of the present disclosure;

FIG. 6D shows a schematic view of the surgical instrument guiding picture on the displaying device for checking the second surgical instrument according to the second embodiment of the present disclosure; and FIG. 6E shows a schematic view of the surgical instrument guiding picture on the displaying device for guiding the second surgical instrument according to the second embodiment of the present disclosure.

DETAILED DESCRIPTION

Figure 1:
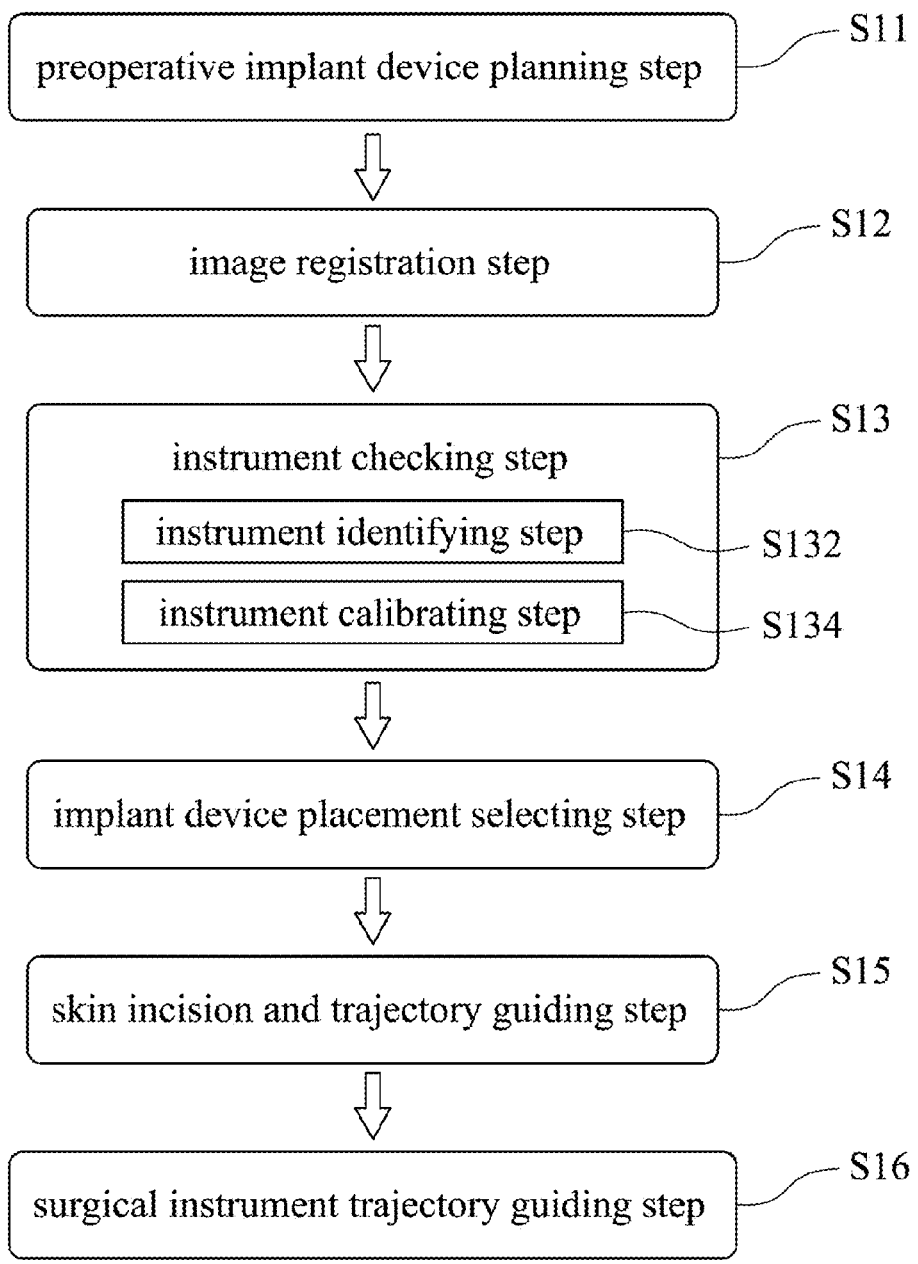
FIG. 1 shows a flow chart of a no-touch surgical navigation method for guiding a surgical instrument corresponding to a part of a patient's anatomy according to a first embodiment of the present disclosure.
Figure 2A:
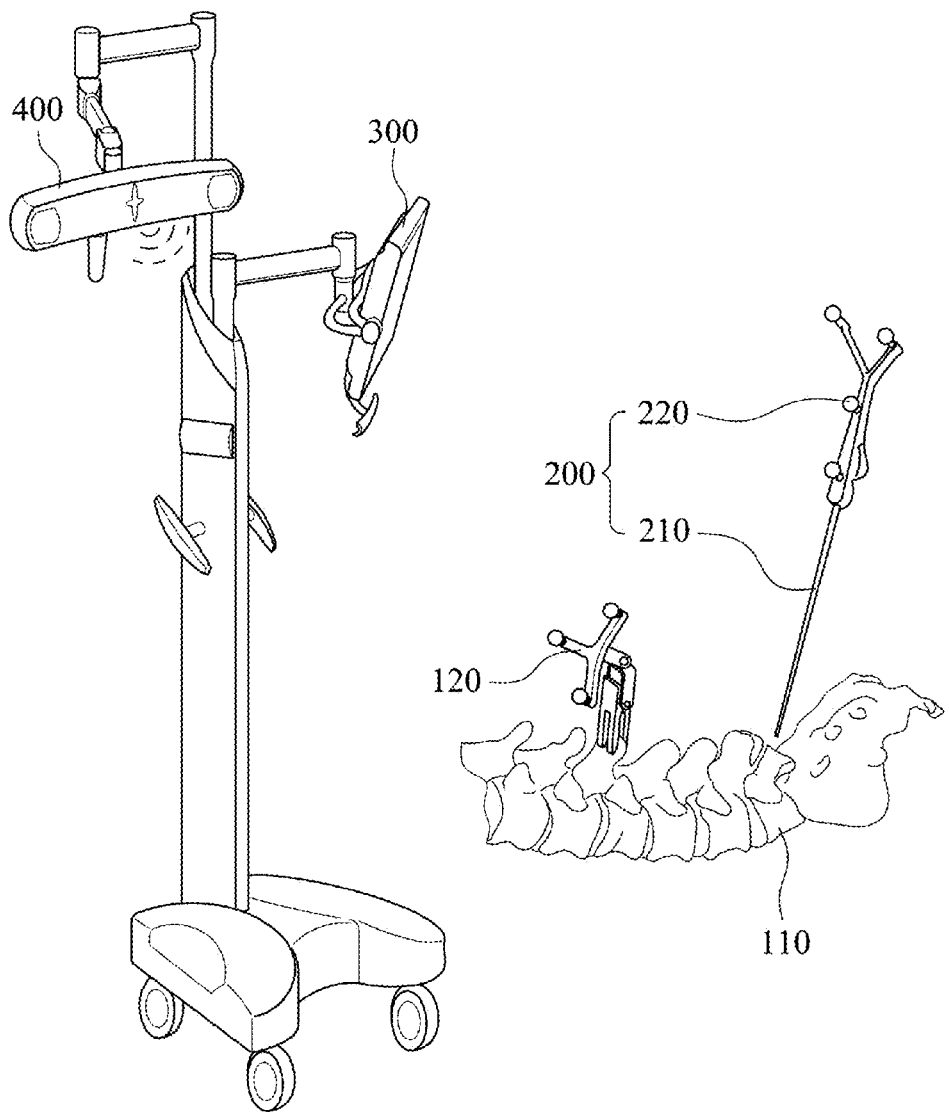
FIG. 2A shows a schematic view of a no-touch surgical navigation system for guiding the surgical instrument corresponding to the part of the patient's anatomy according to the first embodiment of the present disclosure.
Figure 2B:
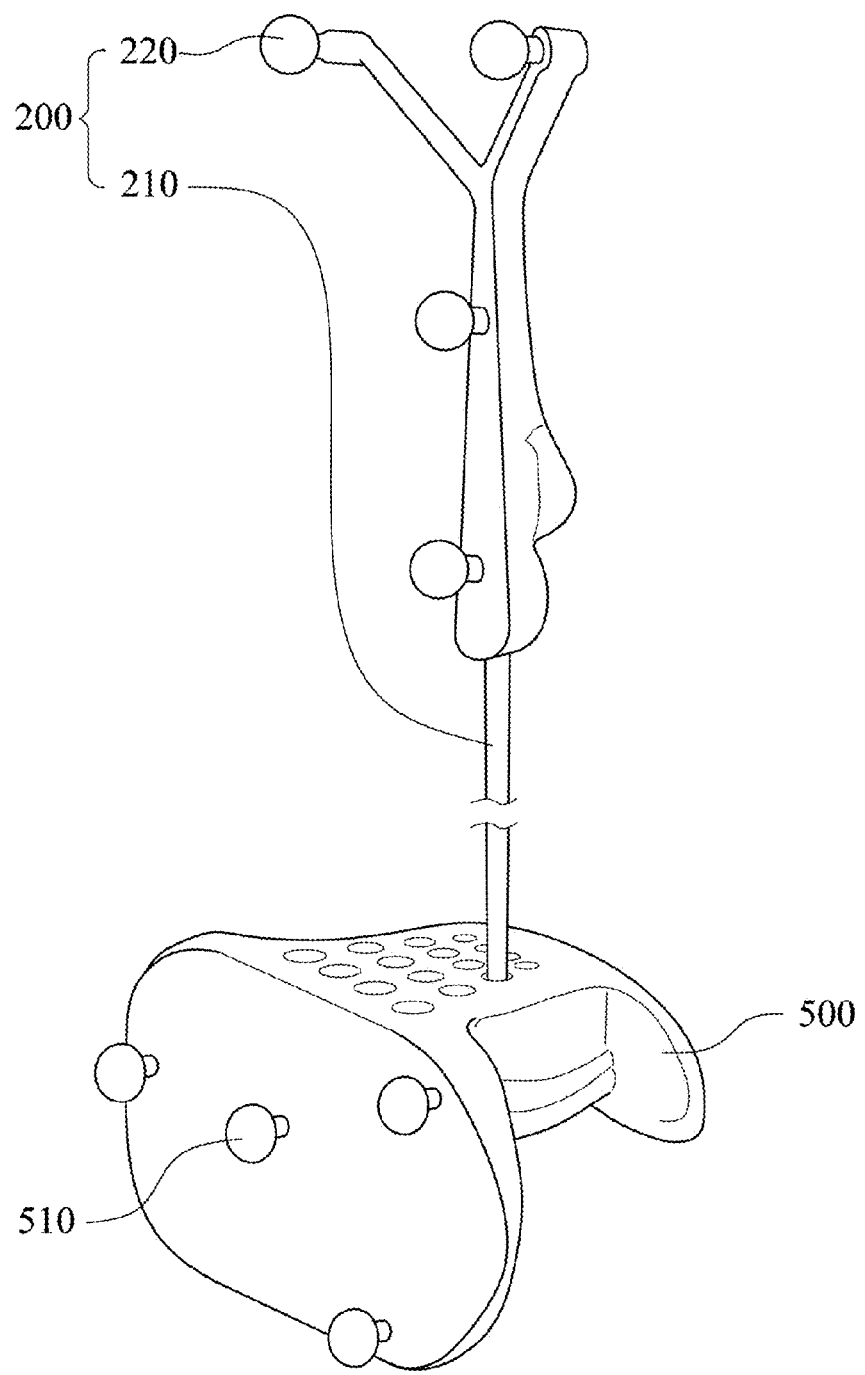
FIG. 2B shows a schematic view of the surgical instrument cooperated with a calibrating device according to the first embodiment of the present disclosure.
Figure 2C:
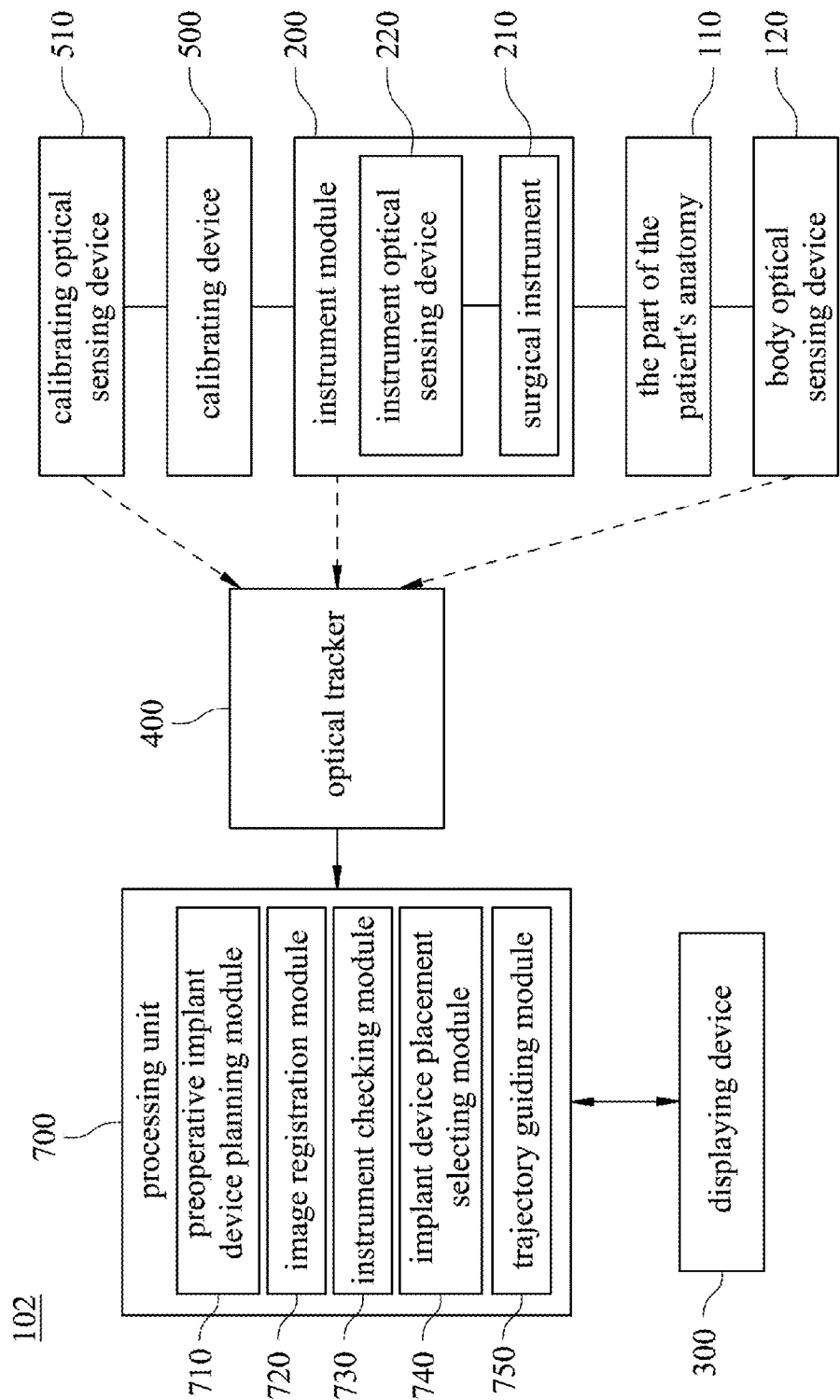
FIG. 2C shows a block diagram of the no-touch surgical navigation system according to the first embodiment of the present disclosure.
Figure 3A:
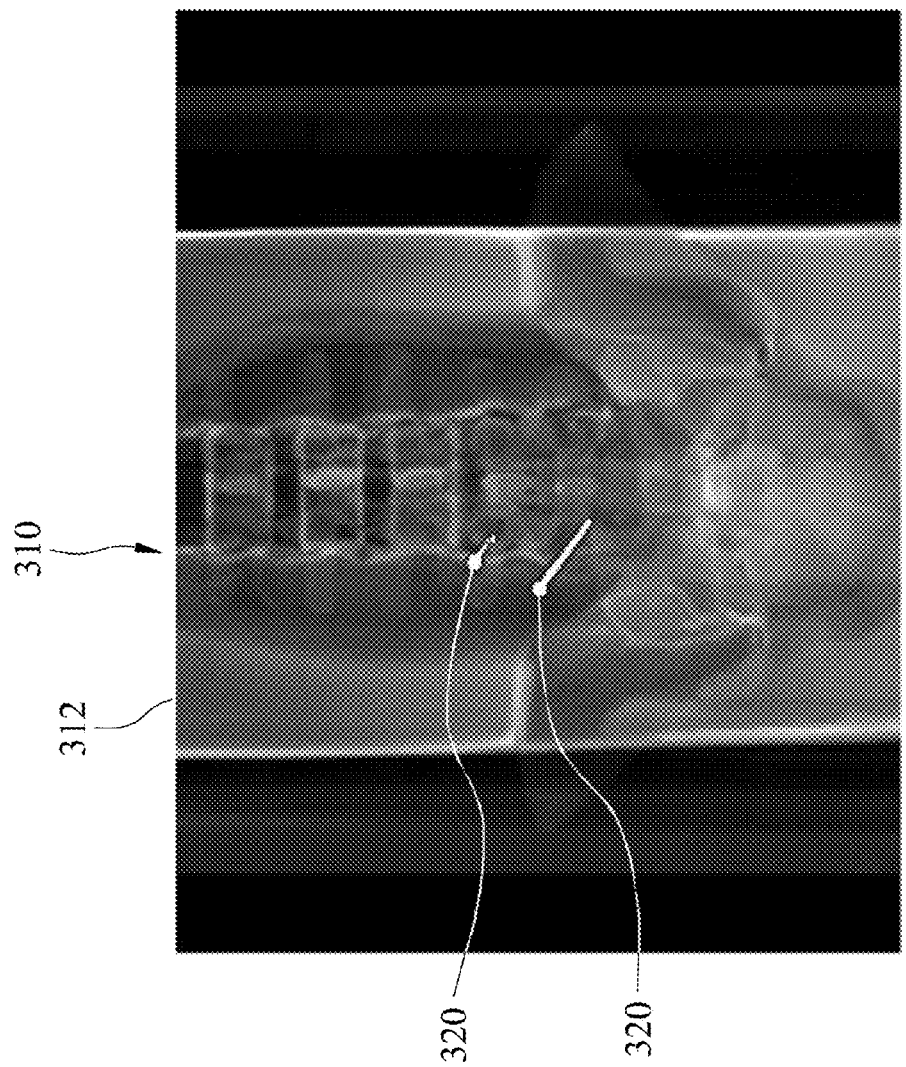
FIG. 3A shows a schematic view of a preoperative implant device planning image on a displaying device according to the first embodiment of the present disclosure.
Figure 3C:
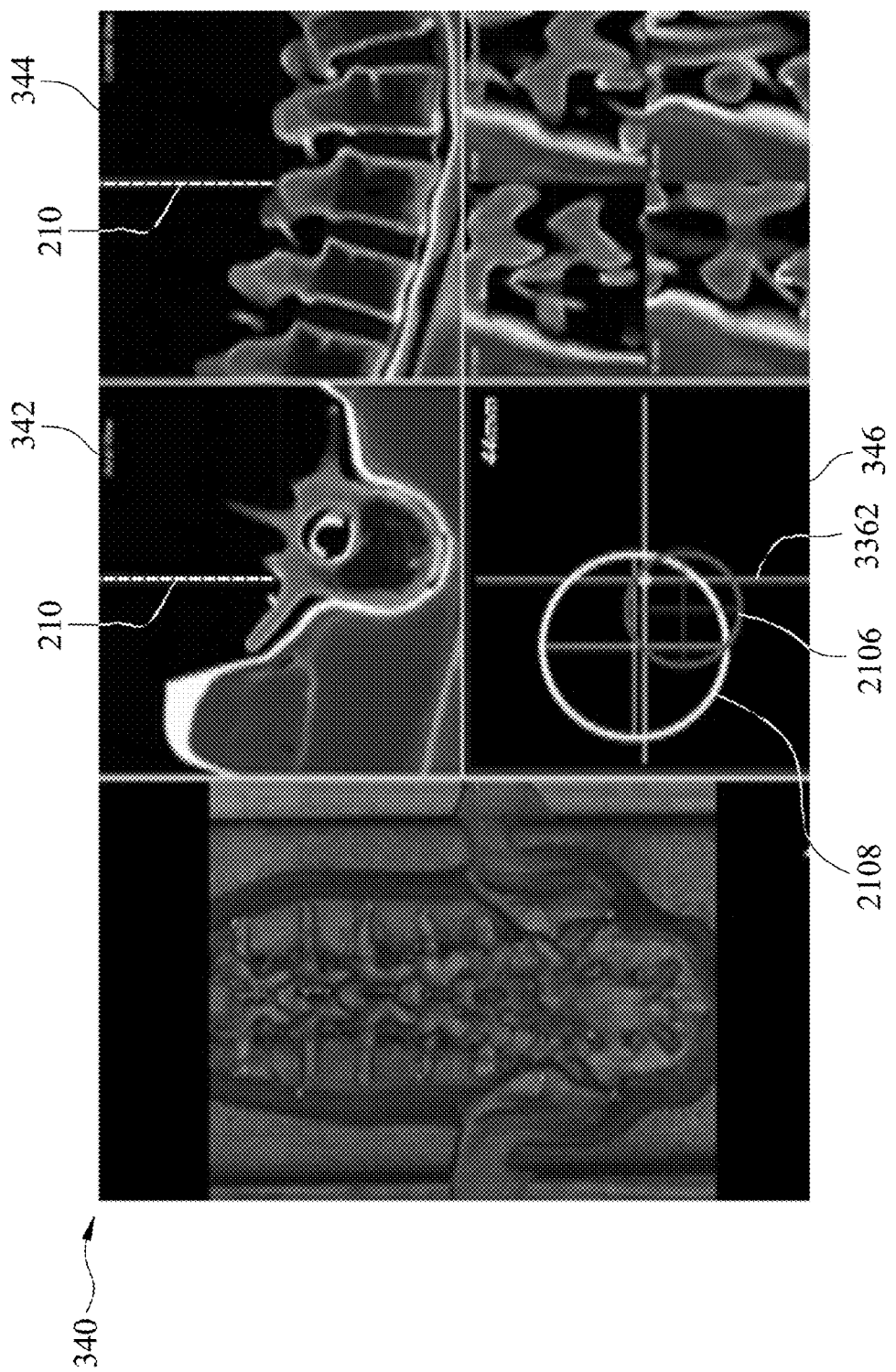
FIG. 3C shows a schematic view of a surgical instrument guiding picture on the displaying device according to the first embodiment of the present disclosure.

FIG. 1 shows a flow chart of a no-touch surgical navigation method 100 for guiding a surgical instrument 210 corresponding to a part of a patient's anatomy 110 according to a first embodiment of the present disclosure; FIG. 2A shows a schematic view of a no-touch surgical navigation system 102 for guiding the surgical instrument 210 corresponding to the part of the patient's anatomy 110 according to the first embodiment of the present disclosure; FIG. 2B shows a schematic view of the surgical instrument 210 cooperated with a calibrating device 500 according to the first embodiment of the present disclosure; FIG. 2C shows a block diagram of the no-touch surgical navigation system 102 according to the first embodiment of the present disclosure; FIG. 3A shows a schematic view of a preoperative implant device planning image 310 on a displaying device 300 according to the first embodiment of the present disclosure; FIG. 3B shows a schematic view of a skin incision and trajectory guiding picture 330 on the displaying device 300 according to the first embodiment of the present disclosure; and FIG. 3C shows a schematic view of a surgical instrument guiding picture 340 on the displaying device 300 according to the first embodiment of the present disclosure. The no-touch surgical navigation method 100 is utilized for guiding the surgical instrument 210 corresponding to the part of the patient's anatomy 110. The surgical instrument 210 may be a guiding probe or a bone screw, and the part of the patient's anatomy 110 may be a vertebral body. The no-touch surgical navigation method 100 provides a preoperative implant device planning step S11, an image registration step S12, an instrument checking step S13, an implant device placement selecting step S14, a skin incision and trajectory guiding step S15 and a surgical instrument trajectory guiding step S16.

The preoperative implant device planning step S11 is for acquiring at least one preoperative implant device planning image 310 and visualizing the preoperative implant device planning image 310 on the displaying device 300, as shown in FIG. 3A. In detail, the preoperative implant device planning image 310 includes a preoperative patient anatomical image 312 and a virtual surgical instrument pattern 320. In the case of spinal surgery, the preoperative patient anatomical image 312 is a three-dimensional medical image of the vertebral body of the patient which is reconstructed after the part of the patient's anatomy 110 scanned by a computed tomography (CT) scan. The virtual surgical instrument pattern 320 is a bone screw pattern. After the preoperative patient anatomical image 312 obtain by the CT scan, the user can plan the specification and placement of an implant device (i.e., the surgical instrument 210) according to the preoperative patient anatomical image 312. The specification of the implant device includes the diameter and the length of the surgical instrument 210. The placement of the implant device includes a correct position and a panoramic image of the surgical instrument 210. The specification and placement of the surgical instrument 210 can be stored for reading and reusing. In addition, the preoperative implant device planning step S11 is used for verifying a panoramic image of the surgical instrument 210 (i.e., the implant device) and checking a relative position between the virtual surgical instrument pattern 320 and the preoperative patient anatomical image 312. The preoperative implant device planning step S11 provides a pre-planning interface displaying step, an implant trajectory pattern adding step, an implant trajectory pattern adjusting step and a panoramic image verifying step. The pre-planning interface displaying step is for displaying the preoperative patient anatomical image 312, a menu and a cursor on a screen of the displaying device 300. The implant trajectory pattern adding step is for moving the cursor to select an implant adding item of the menu by a user and then generating the virtual surgical instrument pattern 320 in the preoperative patient anatomical image 312, and the virtual surgical instrument pattern 320 is located at a starting position. The implant trajectory pattern adjusting step is for controlling the cursor to adjust a position of the virtual surgical instrument pattern 320 and then moving the virtual surgical instrument pattern 320 from the starting position to a target position in the preoperative patient anatomical image 312. The panoramic image verifying step is for rotating the preoperative patient anatomical image 312 around the virtual surgical instrument pattern 320 at a viewing angle according to the target position and the virtual surgical instrument pattern 320 as a central axis, and the viewing angle is greater than 0 degrees and smaller than or equal to 180 degrees. When the viewing angle is sequentially changed from 0 degrees to 180 degrees, a first semicircular region surrounding the surgical instrument 210 (0-180 degrees) can be verified by the user, and a second semicircular region surrounding the surgical instrument 210 (180-360 degrees) is reversely symmetrical to the first semicircular region surrounding the surgical instrument 210 (0-180 degrees). Certainly, the viewing angle may be greater than 180 degrees and smaller than or equal to 360 degrees according to the user's needs. In other words, the viewing angle can be sequentially changed from 0 degrees to 360 degrees in order to completely verify panoramic images of the surgical instrument 210. Accordingly, the preoperative implant device planning step S11 of the present disclosure utilizes the 180-degree rotation of the preoperative patient anatomical image 312 around the virtual surgical instrument pattern 320 as the central axis to allow the physician to correctly verify the relative positions of the bone screw (corresponding to the virtual surgical instrument pattern 320) and the vertebral body (corresponding to the preoperative patient anatomical image 312), thereby adaptively correcting the planning path and positions of the surgical instrument 210 to improve the safety and reliability before surgical procedures.

The image registration step S12 is for establishing a spatial coordinate transformation relationship between the part of the patient's anatomy 110 and the preoperative implant device planning image 310, and matching the preoperative implant device planning image 310 and the part of the patient's anatomy 110 via the spatial coordinate transformation relationship. In detail, the image registration step S12 is for building the links between the part of the patient's anatomy 110 and the preoperative implant device planning image 310. The image registration step S12 is for driving a radiographic image capturing system to capture an intraoperative patient anatomical image corresponding to the part of the patient's anatomy 110 and disposing a radiographic optical sensing device on the radiographic image capturing system. A body optical sensing device 120 is disposed on the part of the patient's anatomy 110. In one embodiment, the radiographic image capturing system is a C-arm X-ray machine, and the body optical sensing device 120 includes a plurality of reflective balls and a dynamic reference frame (DRF) connected to the reflective balls. Then, the radiographic optical sensing device and the body optical sensing device 120 are both oriented towards an optical tracker 400 to establish the spatial coordinate transformation relationship between the part of the patient's anatomy 110 and the preoperative implant device planning image 310. The preoperative patient anatomical image 312 is corresponding to the intraoperative patient anatomical image via the spatial coordinate transformation relationship. In other words, the physician takes two or more C-arm pictures via the C-arm X-ray machine to obtain the actual spatial coordinates of the patient during the surgical procedure. Then, the preoperative patient anatomical image 312 of the preoperative implant device planning image 310 is matched with the C-arm pictures through an image registration algorithm of the system, so that the spatial coordinate of the C-arm pictures is consistent with the spatial coordinate of the patient.

The instrument checking step S13 is for identifying the surgical instrument 210, and then calibrating a size of the surgical instrument 210 to display an instrument tip mark (not shown) of the surgical instrument 210 on the displaying device 300. In detail, an instrument module 200 includes the surgical instrument 210 and an instrument optical sensing device 220, as shown in FIG. 2A. The surgical instrument 210 is a guiding probe. The instrument optical sensing device 220 includes four reflective balls and a Y-shaped dynamic reference frame. Moreover, the instrument checking step S13 includes an instrument identifying step S132 and an instrument calibrating step S134. The instrument identifying step S132 is for disposing the instrument optical sensing device 220 on the surgical instrument 210, and the instrument optical sensing device 220 is oriented towards the optical tracker 400 so as to identify the type and specification of the surgical instrument 210 by the optical tracker 400. The instrument calibrating step S134 is for disposing a calibrating optical sensing device 510 on the calibrating device 500, and then engaging the surgical instrument 210 with the calibrating device 500, and orienting the surgical instrument 210 and the calibrating device 500 towards the optical tracker 400. The surgical instrument 210 of the instrument module 200 and the calibrating device 500 are simultaneously identified by the optical tracker 400 to establish a spatial coordinate transformation relationship between a tip of the surgical instrument 210 and the instrument optical sensing device 220. In other words, the optical tracker 400 simultaneously detects the four reflective balls of the instrument optical sensing device 220 and the four reflective balls of the calibrating optical sensing device 510 of the calibrating device 500 to obtain a precise position of the tip of the surgical instrument 210 in space by the eight reflective balls of the instrument optical sensing device 220 and the calibrating device 500. The precise position of the tip of the surgical instrument 210 is presented on the displaying device 300, as shown in FIG. 2B.

The implant device placement selecting step S14 is for moving the surgical instrument 210 by the user, and the instrument tip mark is synchronously moved with the surgical instrument 210 to select a virtual surgical instrument pattern 320 in the preoperative implant device planning image 310. Then, a skin incision and trajectory guiding picture 330 is shown on the displaying device 300, as shown in FIG. 3A. In detail, the implant device placement selecting step S14 is for moving the surgical instrument 210 by the user to move the instrument tip mark corresponding to a position of the tip of the surgical instrument 210 in the preoperative implant device planning image 310. When the instrument tip mark is moved to a position of the virtual surgical instrument pattern 320, the preoperative implant device planning image 310 is changed to the skin incision and trajectory guiding picture 330 on the displaying device 300.

The skin incision and trajectory guiding step S15 is for moving the surgical instrument 210 by the user according to the skin incision and trajectory guiding picture 330 so as to move the instrument tip mark close to a planned surgical position 3362, and the planned surgical position 3362 is displayed in the skin incision and trajectory guiding picture 330, as shown in FIG. 3B. The skin incision and trajectory guiding picture 330 includes a transverse plane 332, a sagittal plane 334 and a skin incision aiming image 336. The transverse plane 332 is defined by an area between an x-axis and a z-axis. The virtual surgical instrument pattern 320 and the instrument tip mark 2102 are displayed at a first viewing angle in the transverse plane 332. The sagittal plane 334 is defined by an area between the z-axis and a y-axis. The x-axis, the y-axis and the z-axis define a surgical site coordinate system, and the virtual surgical instrument pattern 320 and the instrument tip mark 2102 are displayed at a second viewing angle in the sagittal plane 334. The position of the virtual surgical instrument pattern 320 is corresponding to the planned surgical position 3362. The skin incision aiming image 336 displays the instrument tip mark 2104 and the planned surgical position 3362. The instrument tip mark 2102 of the transverse plane 332, the instrument tip mark 2102 of the sagittal plane 334 and the instrument tip mark 2104 of the skin incision aiming image 336 are simultaneously moved with the movement of the surgical instrument 210 according to the surgical site coordinate system. In other words, the instrument tip mark 2102 of the transverse plane 332, the instrument tip mark 2102 of the sagittal plane 334 and the instrument tip mark 2104 of the skin incision aiming image 336 are moved according to the movement of the surgical instrument 210 and respective coordinates. Additionally, in the skin incision aiming image 336 of the skin incision and trajectory guiding picture 330, there is a distance between the instrument tip mark 2104 and the planned surgical position 3362. When the distance is greater than a first predetermined distance value, the instrument tip mark 2104 is displayed in a first color being red. When the distance is smaller than or equal to the first predetermined distance value and greater than a second predetermined distance value, the instrument tip mark 2104 is displayed in a second color being yellow. When the distance is smaller than or equal to the second predetermined distance value, the instrument tip mark 2104 is displayed in a third color being green, so that the first color, the second color and the third color are different from each other. Furthermore, the skin incision and trajectory guiding step S15 is for moving the surgical instrument 210 by the user to align the instrument tip mark 2104 with the planned surgical position 3362 in the skin incision and trajectory guiding picture 330. When the instrument tip mark 2104 is fully aligned with the planned surgical position 3362 for a period of time (e.g., 0.5 seconds to 1 second), the skin incision and trajectory guiding picture 330 is changed to a surgical instrument guiding picture 340 on the displaying device 300.

The surgical instrument trajectory guiding step S16 is for moving a tip and a tail of the surgical instrument 210 close to the planned surgical position 3362 according to the surgical instrument guiding picture 340, and then the tip and the tail of the surgical instrument 210 are simultaneously aligned with the planned surgical position 3362, as shown in FIG. 3C. The surgical instrument guiding picture 340 includes a transverse plane 342, a sagittal plane 344 and an instrument aiming image 346. The detail of the transverse plane 342 and the sagittal plane 344 are the same as the transverse plane 332 and the sagittal plane 334 of the skin incision and trajectory guiding picture 330. The instrument aiming image 346 includes an instrument tip mark 2106, an instrument tail mark 2108 and the planned surgical position 3362, so that the surgical instrument guiding picture 340 displays the instrument tip mark 2106, the instrument tail mark 2108 and the planned surgical position 3362. The instrument tip mark 2106 is corresponding to the tip of the surgical instrument 210 and spaced from the planned surgical position 3362 by a tip distance. The instrument tail mark 2108 is corresponding to the tail of the surgical instrument 210 and spaced from the planned surgical position 3362 by a tail distance. When the tip distance is greater than the first predetermined distance value, the instrument tip mark 2106 is displayed in the first color being red. When the tail distance is greater than the first predetermined distance value, the instrument tail mark 2106 is displayed in the first color being red. When the tip distance is smaller than or equal to the first predetermined distance value and greater than the second predetermined distance value, the instrument tip mark 2106 is displayed in the second color being yellow. When the tail distance is smaller than or equal to the first predetermined distance value and greater than a second predetermined distance value, the instrument tail mark 2108 is displayed in the second color being yellow. When the tip distance is smaller than or equal to the second predetermined distance value, the instrument tip mark 2106 is displayed in the third color being green. When the tail distance is smaller than or equal to the second predetermined distance value, the instrument tail mark 2108 is displayed in the third color being green. The first color, the second color and the third color are different from each other. If the instrument tip mark 2106 and the instrument tail mark 2108 are both displayed in the green color, it represents that the user (physician) operates the surgical instrument 210 in the correct position. The first predetermined distance value and the second predetermined distance value can be freely set by the user according to requirements of the surgery. Therefore, the no-touch surgical navigation method 100 of the present disclosure uses plural specific steps to reduce redundant touch of the physician when the physician controls the surgical instrument 210 during the surgical procedure, thus improving convenience and efficiency of use.

In FIGS. 1-3C, a no-touch surgical navigation system 102 using the no-touch surgical navigation method 100 can control the surgical instrument 210 to immediately move to the correct position. A body optical sensing device 120 is disposed on the part of the patient's anatomy 110. The no-touch surgical navigation system 102 includes an instrument module 200, a displaying device 300, an optical tracker 400, a calibrating device 500 and a processing unit 700.

The instrument module 200 includes the surgical instrument 210 and the instrument optical sensing device 220. The surgical instrument 210 is moved by the user and connected to the instrument optical sensing device 220. The surgical instrument 210 may be the guiding probe, the bone screw or other surgical instrument according to the user's selection and requirement.

The displaying device 300 includes a screen which displays a preoperative implant device planning image 310, a virtual surgical instrument pattern 320, a skin incision and trajectory guiding picture 330 or a surgical instrument guiding picture 340.

The optical tracker 400 is used for tracking the part of the patient's anatomy, the surgical instrument 210 and the calibrating device 500. When the user (e.g., a physician) controls the surgical instrument 210, the optical tracker 400 is configured to sense the instrument optical sensing device 220, and the instrument optical sensing device 220 is oriented towards the optical tracker 400 so as to identify the surgical instrument 210 by the optical tracker 400 and obtain a surgical instrument datum corresponding to the surgical instrument 210. The surgical instrument datum includes the type and specification of the surgical instrument 210. In addition, the body optical sensing device 120 is also oriented towards the optical tracker 400 so as to identify the precision position of the part of the patient's anatomy 110 and the relative position between the part of the patient's anatomy 110 and the surgical instrument 210 by the optical tracker 400.

The calibrating device 500 is detachably connected to the surgical instrument 210. The calibrating device 500 has a plurality of calibrating holes which have different diameters. These different diameters range from about 2 mm to about 10.5 mm, and may be corresponding to various diameters of bone screws or guiding probes, as shown in FIG. 6D. The calibrating optical sensing device 510 is disposed on the calibrating device 500 oriented towards the optical tracker 400, thus identifying the precision position of the tip of the surgical instrument 210 via the optical tracker 400. Moreover, if the instrument optical sensing device 220, the calibrating optical sensing device 510 and the body optical sensing device 120 are simultaneously oriented towards the optical tracker 400, the relative positions of the calibrating device 500, the surgical instrument 210 and the preoperative implant device planning image 310 can be obtained by the optical tracker 400.

The processing unit 700 is signally connected to the displaying device 300 and the optical tracker 400. The processing unit 700 may be a computer, a cloud processor or a mobile device. The processing unit 700 includes a preoperative implant device planning module 710, an image registration module 720, an instrument checking module 730, an implant device placement selecting module 740 and a trajectory guiding module 750. The preoperative implant device planning module 710, the image registration module 720, an instrument checking module 730, an implant device placement selecting module 740 or a trajectory guiding module 750 may be an integrated microchip or a microprocessor. Moreover, the preoperative implant device planning module 710 is utilized to perform the preoperative implant device planning step S11. The preoperative implant device planning module 710 is configured to acquire the preoperative implant device planning image 310 and visualize the preoperative implant device planning image 310 on the screen of the displaying device 300. The image registration module 720 is utilized to perform the image registration step S12 and is signally connected to the preoperative implant device planning module 710. The image registration module 720 is configured to establish the spatial coordinate transformation relationship between the part of the patient's anatomy 110 and the preoperative implant device planning image 310, and match the preoperative implant device planning image 310 and the part of the patient's anatomy 110 via the spatial coordinate transformation relationship. The instrument checking module 730 is utilized to perform the instrument checking step S13 and is signally connected to the image registration module 720 and the screen of the displaying device 300. The instrument checking module 730 is configured to receive the surgical instrument datum and identify a position of the surgical instrument 210 on the screen, and then calibrate the size of the surgical instrument to display the instrument tip mark of the surgical instrument 210 on the screen. Furthermore, the implant device placement selecting module 740 is utilized to perform the implant device placement selecting step S14 and is signally connected to the instrument checking module 730 and the image registration module 720. The implant device placement selecting module 740 is configured to select the virtual surgical instrument pattern 320 in the preoperative implant device planning image 310 by moving the instrument tip mark of the surgical instrument 210 so as to display the skin incision and trajectory guiding picture 330 on the screen of the displaying device 300. The trajectory guiding module 750 is utilized to perform the skin incision and trajectory guiding step S15 and is signally connected to the instrument checking module 730 and the implant device placement selecting module 740. The trajectory guiding module 750 is configured to move the instrument tip mark 2106 close to the planned surgical position 3362 by moving the surgical instrument 210 according to the skin incision and trajectory guiding picture 330 on the screen. Hence, the no-touch surgical navigation system 102 can utilize plural kinds of optical sensing devices combined with the optical tracker 400 to reduce redundant touch of the physician when the physician controls the surgical instrument 210 during the surgical procedure, thereby improving convenience and efficiency of use. Additionally, the no-touch surgical navigation system 102 can use the instrument optical sensing device 220 cooperated with the calibrating device 500 to enhance accuracy and safety of the surgical instrument 210 operated by the physician.

Figure 4:
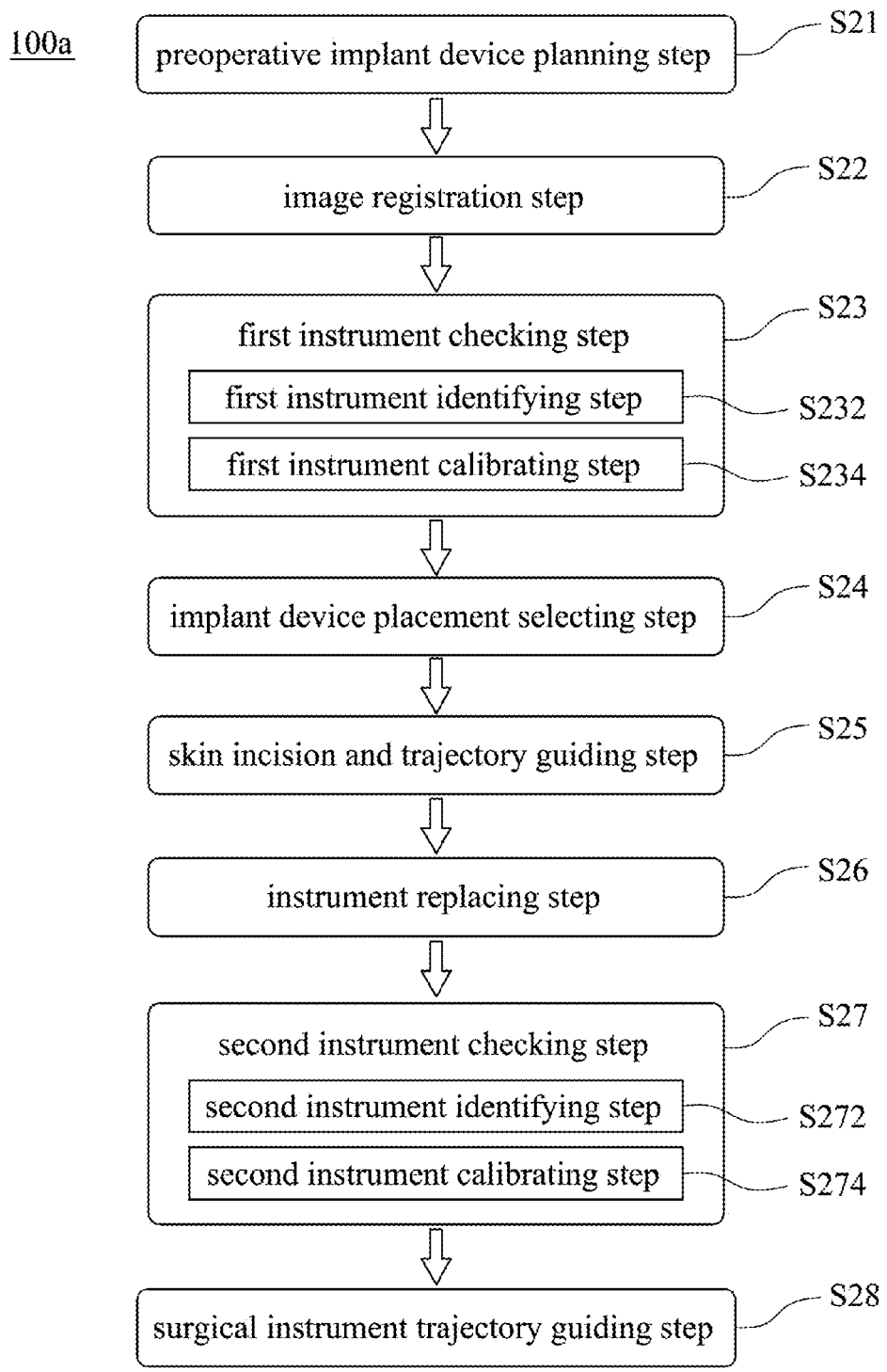
FIG. 4 shows a flow chart of a no-touch surgical navigation method for guiding a plurality of surgical instruments corresponding to a part of a patient's anatomy according to a second embodiment of the present disclosure.
Figure 5A:
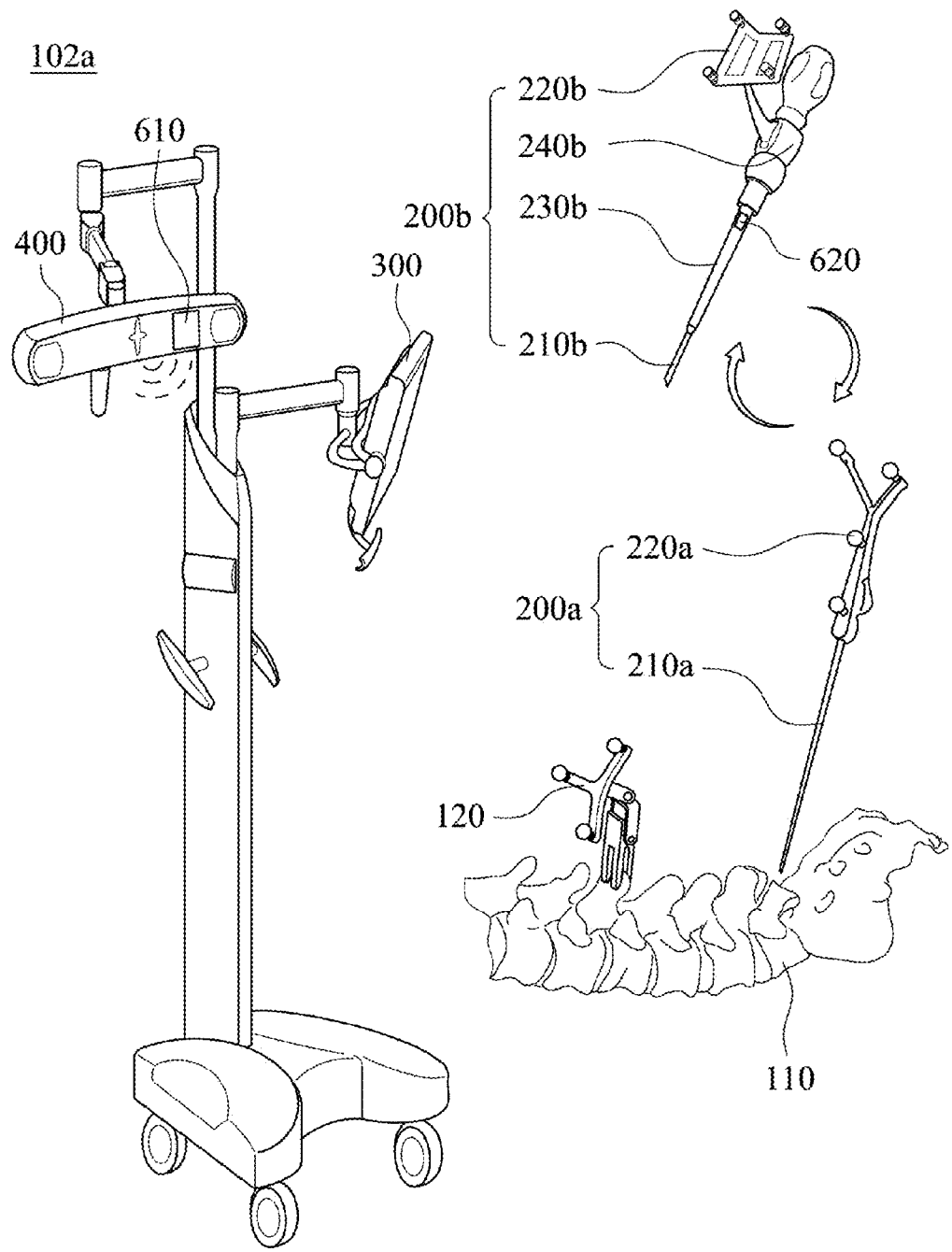
FIG. 5A shows a schematic view of a no-touch surgical navigation system for guiding the surgical instruments corresponding to the part of the patient's anatomy according to the second embodiment of the present disclosure.
Figure 5B:
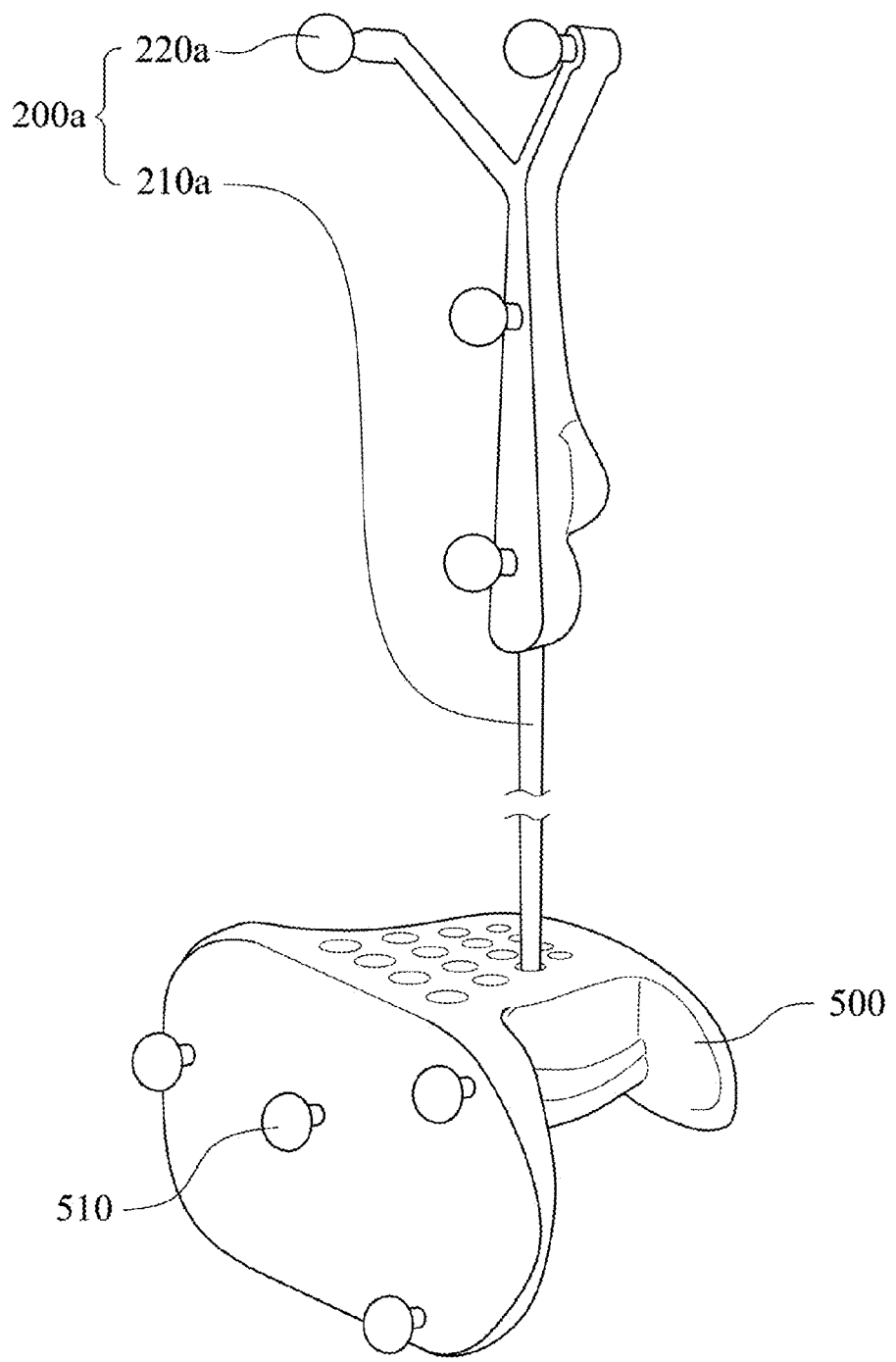
FIG. 5B shows a schematic view of a first surgical instrument cooperated with a calibrating device according to the second embodiment of the present disclosure.
Figure 5C:
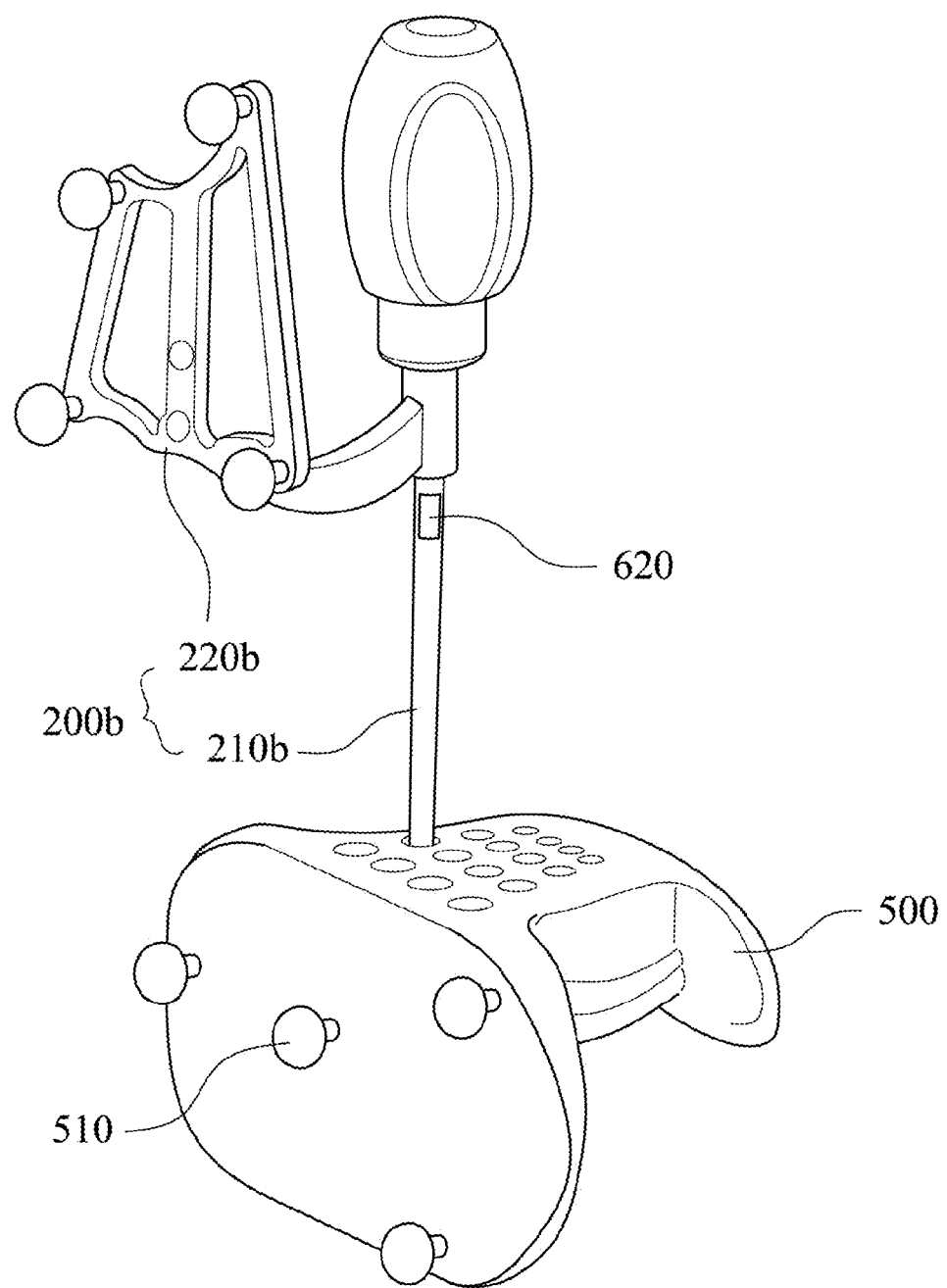
FIG. 5C shows a schematic view of a second surgical instrument cooperated with the calibrating device according to the second embodiment of the present disclosure.
Figure 5D:
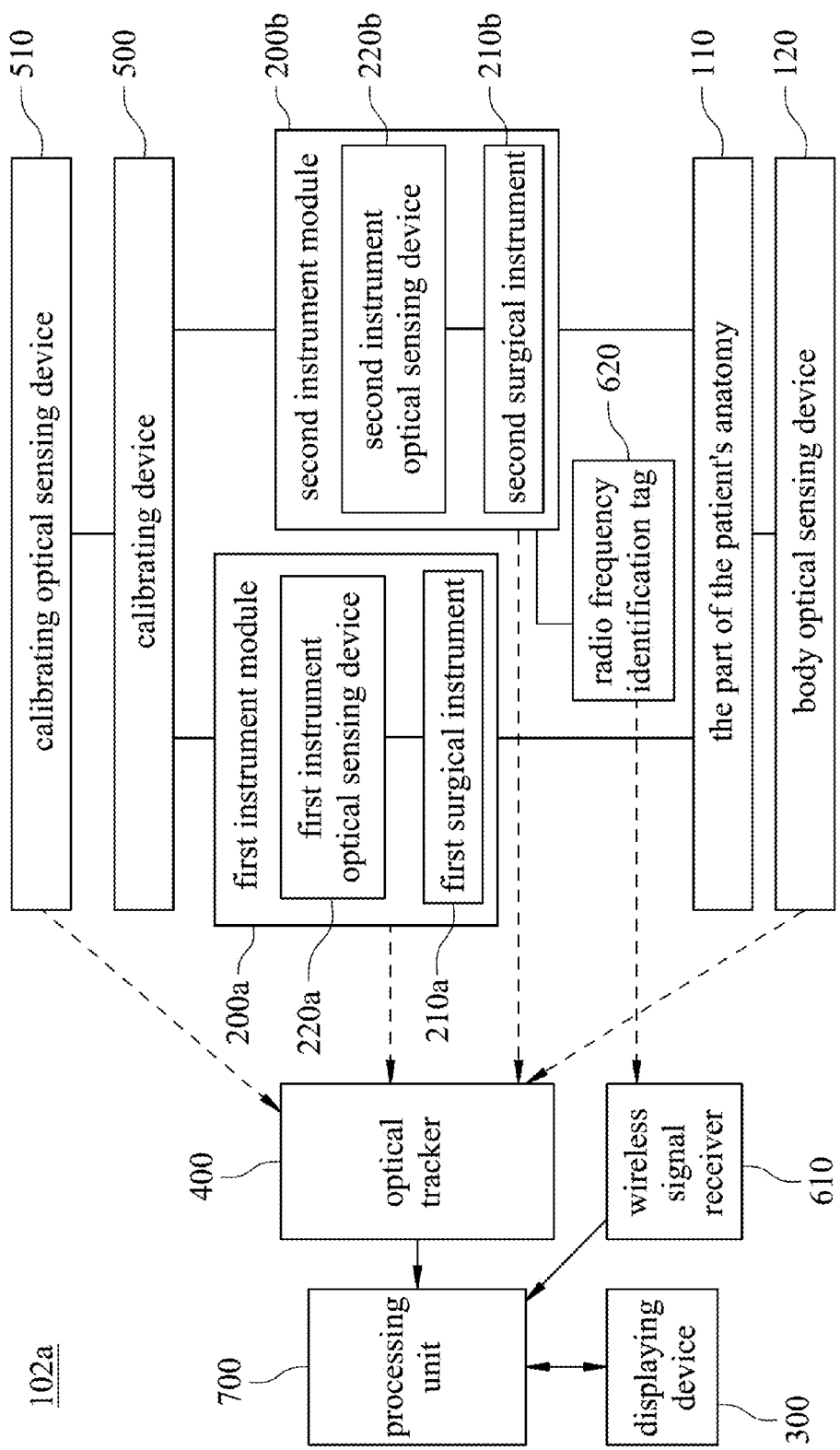
FIG. 5D shows a block diagram of the no-touch surgical navigation system according to the second embodiment of the present disclosure.
Figure 6A:
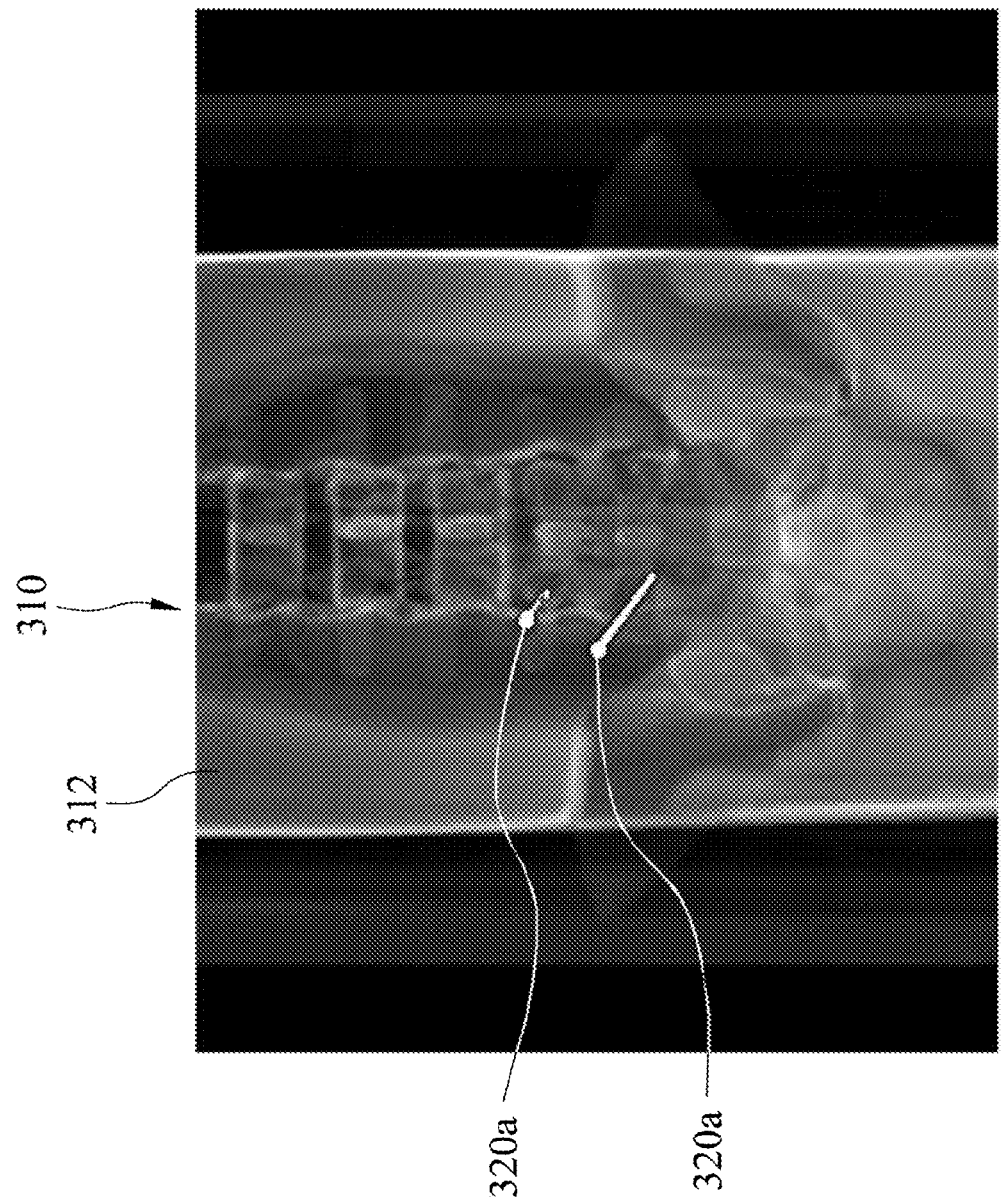
FIG. 6A shows a schematic view of a preoperative implant device planning image on a displaying device according to the second embodiment of the present disclosure.
Figure 6B:
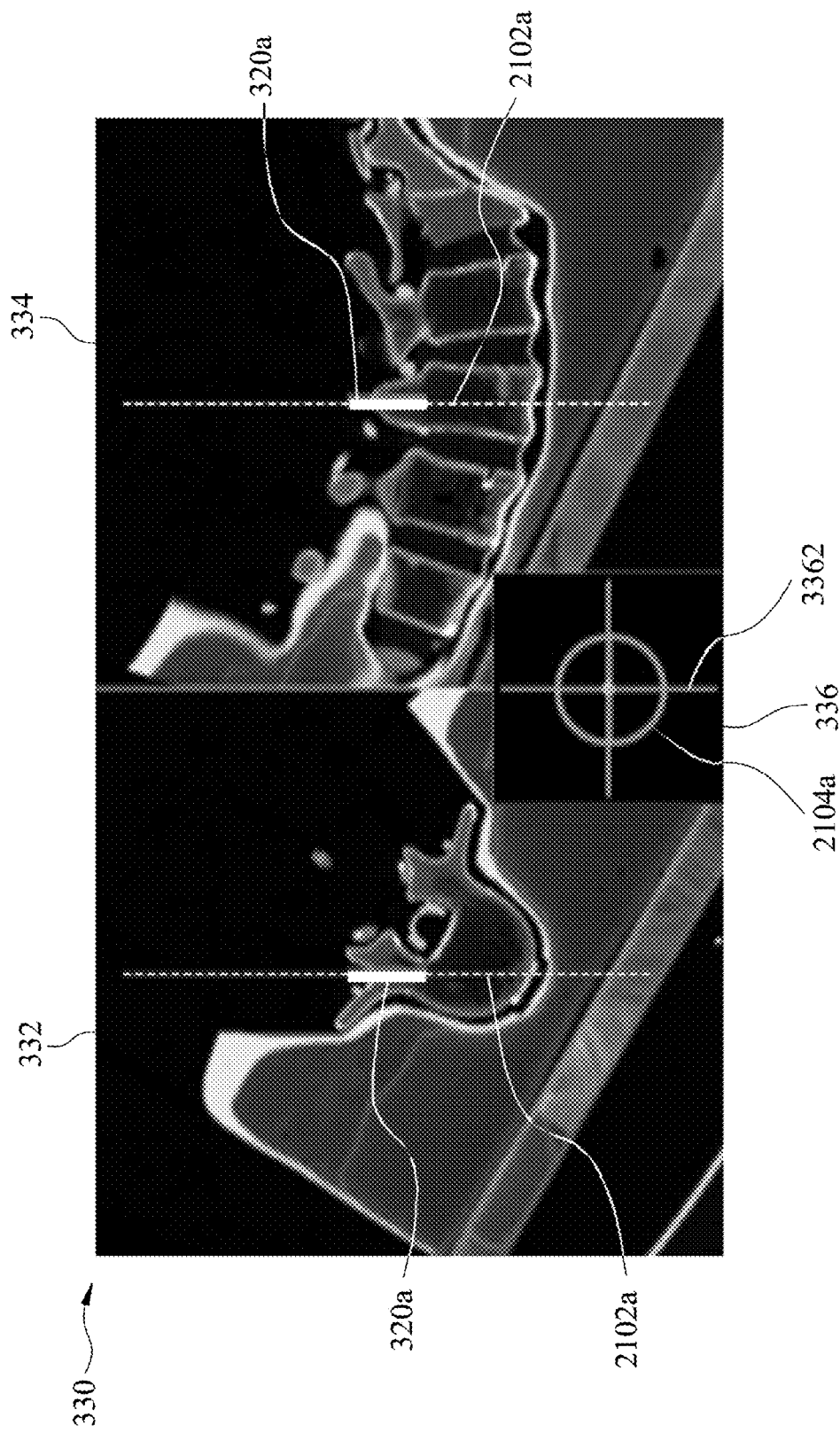
FIG. 6B shows a schematic view of a skin incision and trajectory guiding picture on the displaying device according to the second embodiment of the present disclosure.

FIG. 4 shows a flow chart of a no-touch surgical navigation method 100a for guiding a plurality of surgical instruments corresponding to a part of a patient's anatomy 110 according to a second embodiment of the present disclosure; FIG. 5A shows a schematic view of a no-touch surgical navigation system 102a for guiding the surgical instruments corresponding to the part of the patient's anatomy 110 according to the second embodiment of the present disclosure; FIG. 5B shows a schematic view of a first surgical instrument 210a cooperated with a calibrating device 500 according to the second embodiment of the present disclosure; FIG. 5C shows a schematic view of a second surgical instrument 210b cooperated with the calibrating device 500 according to the second embodiment of the present disclosure; FIG. 5D shows a block diagram of the no-touch surgical navigation system 102a according to the second embodiment of the present disclosure; FIG. 6A shows a schematic view of a preoperative implant device planning image 310 on a displaying device 300 according to the second embodiment of the present disclosure; FIG. 6B shows a schematic view of a skin incision and trajectory guiding picture 330 on the displaying device 300 according to the second embodiment of the present disclosure; FIG. 6C shows a schematic view of a surgical instrument guiding picture 340 on the displaying device 300 for guiding the first surgical instrument 210a according to the second embodiment of the present disclosure; FIG. 6D shows a schematic view of the surgical instrument guiding picture 340 on the displaying device 300 for checking the second surgical instrument 210b according to the second embodiment of the present disclosure; and FIG. 6E shows a schematic view of the surgical instrument guiding picture 340 on the displaying device 300 for guiding the second surgical instrument 210b according to the second embodiment of the present disclosure. The no-touch surgical navigation method 100a for guiding a plurality of surgical instruments corresponding to the part of the patient's anatomy 110. The surgical instruments include the first surgical instrument 210a and the second surgical instrument 210b. The first surgical instrument 210a is a guiding probe, and the second surgical instrument 210b is a bone screw. The no-touch surgical navigation method 100a provides a preoperative implant device planning step S21, an image registration step S22, a first instrument checking step S23, an implant device placement selecting step S24, a skin incision and trajectory guiding step S25, an instrument replacing step S26, a second instrument checking step S27 and a surgical instrument trajectory guiding step S28.

The preoperative implant device planning step S21 is for acquiring at least one preoperative implant device planning image 310 and visualizing the preoperative implant device planning image 310 on the displaying device 300. The detail of the preoperative implant device planning step S21 is the same as the preoperative implant device planning step S11 in FIG. 1.

The image registration step S22 is for establishing a spatial coordinate transformation relationship between the part of the patient's anatomy 110 and the preoperative implant device planning image 310, and matching the preoperative implant device planning image 310 and the part of the patient's anatomy 110 via the spatial coordinate transformation relationship. The detail of the image registration step S22 is the same as the image registration step S12 in FIG. 1.

The first instrument checking step S23 is for identifying the first surgical instrument 210a, and then calibrating a size of the first surgical instrument 210a to display a first instrument tip mark of the first surgical instrument 210a on the displaying device 300. The first instrument tip mark represents a mouse cursor on a screen. The first instrument checking step S23 provides a first instrument identifying step S232 and a first instrument calibrating step S234. The first instrument calibrating step S232 is for disposing a first instrument optical sensing device 220a on the first surgical instrument 210a, and the first instrument optical sensing device 220a is oriented towards an optical tracker 400 so as to identify the first surgical instrument 210a by the optical tracker 400, as shown in FIG. 5A. The first instrument calibrating step S234 is for disposing a calibrating optical sensing device 510 on the calibrating device 500, and then engaging the first surgical instrument 210a with the calibrating device 500, and orienting the first surgical instrument 210a and the calibrating device 500 towards the optical tracker 400. The first surgical instrument 210a and the calibrating device 500 are simultaneously identified by the optical tracker 400 to establish a spatial coordinate transformation relationship between a tip of the first surgical instrument 210a and the first instrument optical sensing device 220a. The reason why the first instrument checking step S23 is performed in the no-touch surgical navigation method 100a is that the tip of the first surgical instrument 210a may be skewed after being used for a certain period of time, and the first instrument checking step S23 can provide precise identification and calibration of the first surgical instrument 210a before a navigation procedure. The first surgical instrument 210a which has been identified and calibrated via the first instrument checking step S23 meets the stringent requirements of surgery and achieves the required accuracy so as to preserve the correctness and safety of surgery in the navigation procedure.

The implant device placement selecting step S24 is for moving the first surgical instrument 210a by the user, and the first instrument tip mark is synchronously moved with the first surgical instrument 210a to select a virtual second surgical instrument pattern 320a in the preoperative implant device planning image 310. Then, a skin incision and trajectory guiding picture 330 is shown on the displaying device 300, as shown in FIG. 6A. In other words, the implant device placement selecting step S24 is for moving the first surgical instrument 210a by the user to move the first instrument tip mark corresponding to a position of the tip of the first surgical instrument 210a in the preoperative implant device planning image 310. The first instrument tip mark represents a mouse cursor on the screen. When the first instrument tip mark is moved to a position of the virtual second surgical instrument pattern 320a, the preoperative implant device planning image 310 is changed to the skin incision and trajectory guiding picture 330 on the displaying device 300. In FIG. 6A, the virtual second surgical instrument pattern 320a is a virtual bone screw.

The skin incision and trajectory guiding step S25 is for moving the first surgical instrument 210a by the user according to the skin incision and trajectory guiding picture 330 so as to move the first instrument tip mark 2104a close to a planned surgical position 3362. The planned surgical position 3362 is displayed in the skin incision and trajectory guiding picture 330, as shown in FIG. 6B. When the first instrument tip mark 2104a is aligned with the planned surgical position 3362, the skin incision and trajectory guiding picture 330 is changed to a surgical instrument guiding picture 340 on the displaying device 300, as shown in FIG. 6C. In detail, when the first instrument tip mark 2104a is fully aligned with the planned surgical position 3362 for a period of time, the skin incision and trajectory guiding picture 330 is changed to a surgical instrument guiding picture 340 on the displaying device 300. Additionally, the skin incision and trajectory guiding picture 330 includes a transverse plane 332, a sagittal plane 334 and a skin incision aiming image 336. The transverse plane 332 is defined by an area between an x-axis and a z-axis. The virtual second surgical instrument pattern 320a and the first instrument tip mark 2102a are displayed at a first viewing angle in the transverse plane 332. The sagittal plane 334 is defined by an area between the z-axis and a y-axis. The x-axis, the y-axis and the z-axis define a surgical site coordinate system, and the virtual second surgical instrument pattern 320a and the first instrument tip mark 2102a are displayed at a second viewing angle in the sagittal plane 334. The skin incision aiming image 336 displays the first instrument tip mark 2104a and the planned surgical position 3362. The first instrument tip mark 2102a of the transverse plane 332, the first instrument tip mark 2102a of the sagittal plane 334 and the first instrument tip mark 2104a of the skin incision aiming image 336 are simultaneously moved with the movement of the first surgical instrument 210a according to the surgical site coordinate system, so that it is convenient and expeditious for the physician to know the relative position of the first surgical instrument 210a (i.e., the first instrument tip mark 2104a) and a target position (i.e., the planned surgical position 3362) in the space. Moreover, in the skin incision and trajectory guiding picture 330, there is a distance between the first instrument tip mark 2104a and the planned surgical position 3362. When the distance is greater than a first predetermined distance value, the first instrument tip mark 2104a is displayed in a first color being red. When the distance is smaller than or equal to the first predetermined distance value and greater than a second predetermined distance value, the first instrument tip mark 2104a is displayed in a second color being yellow. When the distance is smaller than or equal to the second predetermined distance value, the first instrument tip mark 2104a is displayed in a third color being green. The size of the distance affects the color of the first instrument tip mark 2104a. In other words, the physician can immediately know the distance via the color of the first instrument tip mark 2104a. The red color represents that the distance is greater than the first predetermined distance value. The yellow color represents that the distance is smaller than or equal to the first predetermined distance value and greater than the second predetermined distance value. The green color represents that the distance is smaller than or equal to the second predetermined distance value. In FIG. 6C, the surgical instrument guiding picture 340 displays a first instrument tip mark 2106a, a first instrument tail mark 2108a and the planned surgical position 3362. The first instrument tip mark 2106a is corresponding to the tip of the first surgical instrument 210a. The first instrument tail mark 2108a is corresponding to the tail of the first surgical instrument 210a. The first instrument tip mark 2106a is spaced from the planned surgical position 3362 by a tip distance, and the first instrument tail mark 2108a is spaced from the planned surgical position 3362 by a tail distance. Accordingly, the skin incision and trajectory guiding step S25 of the present disclosure uses the double marks combined with changeable colors to enable the physician to quickly and accurately move the first surgical instrument 210a to the target position, thereby substantially reducing operating time and improving the safety of surgery.

The instrument replacing step S26 is for replacing the first surgical instrument 210a (i.e., the guiding probe) with the second surgical instrument 210b (i.e., the bone screw) by the user according to the virtual second surgical instrument pattern 320a of the implant device placement selecting step S24. The virtual second surgical instrument pattern 320a is corresponding to the second surgical instrument 210b. After the instrument replacing step S26, the first instrument tip mark 2106a and the first instrument tail mark 2108a of the surgical instrument guiding picture 340 are replaced with a second instrument tip mark 2106b and a second instrument tail mark 2108b, respectively, as shown in FIGS. 6C and 6E.

The second instrument checking step S27 is for identifying the second surgical instrument 210b, and then calibrating a size of the second surgical instrument 210b to display a second instrument tip mark 2106b of the second surgical instrument 210b on the displaying device 300, as shown in FIG. 6D. In detail, the second instrument checking step S27 provides a second instrument identifying step S272 and a second instrument calibrating step S274. The second instrument identifying step S272 is for disposing a second instrument optical sensing device 220b on the second surgical instrument 210b, and the second instrument optical sensing device 220b is oriented towards the optical tracker 400 so as to identify the second surgical instrument 210b by the optical tracker 400. Furthermore, the second instrument identifying step S272 is for disposing a radio frequency identification tag 620 (RFID tag) on the second surgical instrument 210b and driving a wireless signal receiver 610 (RFID reader) to sense the radio frequency identification tag 620 so as to identify the second surgical instrument 210b by the wireless signal receiver 610, as shown in FIG. 6D. In addition, the second instrument calibrating step S274 is for disposing the calibrating optical sensing device 510 on the calibrating device 500, and then engaging the second surgical instrument 210b with the calibrating device 500. After that, the second instrument calibrating step S274 is for orienting the second surgical instrument 210b and the calibrating device 500 towards the optical tracker 400. When the second surgical instrument 210b is engaged with the calibrating device 500, the physician corresponds the second surgical instrument 210b to one of plural holes of the calibrating device 500 having a most appropriate diameter. The most appropriate diameter is equal to or greater than the diameter of the second surgical instrument 210b, as shown in FIG. 6D ("Select diameter"). Finally, the second surgical instrument 210b and the calibrating device 500 are simultaneously identified by the optical tracker 400 to establish a spatial coordinate transformation relationship between a tip of the second surgical instrument 210b and the second instrument optical sensing device 220b. The precise length of the second surgical instrument 210b can be also obtain, as shown in FIG. 6D ("Screw length").

The surgical instrument trajectory guiding step S28 is for moving the second surgical instrument 210b close to the planned surgical position 3362 according to the surgical instrument guiding picture 340, as shown in FIG. 6E. In detail, the surgical instrument trajectory guiding step S28 is for moving the second surgical instrument 210b to fully align the second instrument tip mark 2106b and a second instrument tail mark 2108b with the planned surgical position 3362 according to the surgical instrument guiding picture 340. The second instrument tip mark 2106b is corresponding to a tip of the second surgical instrument 210b, and the second instrument tail mark 2108b is corresponding to a tail of the second surgical instrument 210b. The surgical instrument guiding picture 340 displays the second instrument tip mark 2106b, the second instrument tail mark 2108b and the planned surgical position 3362. The second instrument tip mark 2106b is spaced from the planned surgical position 3362 by a tip distance, and the second instrument tail mark 2108b is spaced from the planned surgical position 3362 by a tail distance. When the tip distance is greater than the first predetermined distance value, the second instrument tip mark 2106b is displayed in the red color. When the tail distance is greater than the first predetermined distance value, the second instrument tail mark 2108b is displayed in the red color. When the tip distance is smaller than or equal to the first predetermined distance value and greater than the second predetermined distance value, the second instrument tip mark 2106b is displayed in the yellow color. When the tail distance is smaller than or equal to the first predetermined distance value and greater than the second predetermined distance value, the second instrument tail mark 2108b is displayed in the yellow color. When the tip distance is smaller than or equal to the second predetermined distance value, the second instrument tip mark 2106b is displayed in the green color. When the tail distance is smaller than or equal to the second predetermined distance value, the second instrument tail mark 2108b is displayed in the green color. It is obvious that the red color, the yellow color and the green color are different from each other. If the physician can control the second surgical instrument 210b to maintain the green color in the second instrument tip mark 2106b and the second instrument tail mark 2108b, it represents that the second surgical instrument 210 is operated in the correct and ideal position, thus satisfying the preoperative planning path and condition.

In FIGS. 2C, 5A, 5B, 5C and 5D, the no-touch surgical navigation system 102a is used for guiding the first surgical instrument 210a and the second surgical instrument 210b relative to the part of the patient's anatomy 110 by the no-touch surgical navigation method 100a. A body optical sensing device 120 is disposed on the part of the patient's anatomy 110. The no-touch surgical navigation system 102a includes a first instrument module 200a, a second instrument module 200b, a displaying device 300, an optical tracker 400, a calibrating device 500, a wireless signal receiver 610, a radio frequency identification tag 620 and a processing unit 700.

In FIG. 5D, the detail of the displaying device 300, the optical tracker 400, the calibrating device 500 and the processing unit 700 are the same as the embodiment of FIG. 2C. In FIG. 5D, the no-touch surgical navigation system 102a further includes the first instrument module 200a, the second instrument module 200b, the wireless signal receiver 610 and the radio frequency identification tag 620. The first instrument module 200a includes a first surgical instrument 210a and a first instrument optical sensing device 220a. The second instrument module 200b includes a second surgical instrument 210b, a second instrument optical sensing device 220b, an instrument assembly 230b and a grip 240b. In FIG. 5A, the first surgical instrument 210a is a guiding probe, and the second surgical instrument 210b is a bone screw. The instrument assembly 230b is a bone screw assembly corresponding to the second surgical instrument 210b. The instrument assembly 230b is connected between the second surgical instrument 210b and the grip 240b. Moreover, the wireless signal receiver 610 is disposed adjacent to the optical tracker 400 and used for detecting the radio frequency identification tag 620. The radio frequency identification tag 620 is disposed on the instrument assembly 230b and carries information of the corresponding type and specification of the second surgical instrument 210b. When the radio frequency identification tag 620 is aligned with the optical tracker 400 within a certain distance range, the wireless signal receiver 610 can identify the corresponding type and specification of the second surgical instrument 210b. Accordingly, the no-touch surgical navigation system 102a and the no-touch surgical navigation method 100a are used to freely replace the suitable surgical instrument under a no-touch condition according to surgical requirements, thereby improving convenience and efficiency and maintaining a high degree of accuracy and safety. The no-touch condition represents that the user does not touch the screen or control panels to adjust the parameters (e.g., the types and specifications of the surgical instruments) of the no-touch surgical navigation system 102a, so that the surgical instruments can automatically identified and calibrated by the no-touch surgical navigation method 100a during the surgical procedure. The no-touch surgical navigation system 102a and the no-touch surgical navigation method 100a are suitable for use in surgery to solve the problems of the conventional navigation system and method that require the user to additionally touch the screen or control panels to adjust the parameters during the surgical procedure.

According to the aforementioned embodiments and examples, the advantages of the present disclosure are described as follows.

1. The no-touch surgical navigation method and the no-touch surgical navigation system thereof of the present disclosure can utilize plural kinds of optical sensing devices combined with the optical tracker to reduce redundant touch of the physician when the physician controls the surgical instruments during the surgical procedure, thereby improving convenience and efficiency of use.

2. The no-touch surgical navigation method and the no-touch surgical navigation system thereof of the present disclosure can use the double marks combined with changeable colors to enable the physician to quickly and accurately move the surgical instrument to the target position, thereby substantially reducing operating time and improving the safety of surgery.

3. The no-touch surgical navigation system and the no-touch surgical navigation system thereof of the present disclosure can use the instrument optical sensing device cooperated with the calibrating device to enhance accuracy and safety of the surgical instrument operated by the physician.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A no-touch surgical navigation method for guiding a surgical instrument corresponding to a part of a patient's anatomy, the no-touch surgical navigation method comprising:
providing a preoperative implant device planning step, wherein the preoperative implant device planning step is for acquiring at least one preoperative implant device planning image and visualizing the preoperative implant device planning image on a displaying device;
providing an image registration step, wherein the image registration step is for establishing a spatial coordinate transformation relationship between the part of the patient's anatomy and the preoperative implant device planning image, and matching the preoperative implant device planning image and the part of the patient's anatomy via the spatial coordinate transformation relationship;
providing an instrument checking step, wherein the instrument checking step is for identifying the surgical instrument, and then calibrating a size of the surgical instrument to display an instrument tip mark of the surgical instrument on the displaying device;
providing an implant device placement selecting step, wherein the implant device placement selecting step is for moving the surgical instrument by a user, and the instrument tip mark is synchronously moved with the surgical instrument to select a virtual surgical instrument pattern in the preoperative implant device planning image, and then a skin incision and trajectory guiding picture is shown on the displaying device; and
providing a skin incision and trajectory guiding step, wherein the skin incision and trajectory guiding step is for moving the surgical instrument by the user according to the skin incision and trajectory guiding picture so as to move the instrument tip mark close to a planned surgical position, and the planned surgical position is displayed in the skin incision and trajectory guiding picture.

2. The no-touch surgical navigation method of claim 1, wherein,
the preoperative implant device planning image includes a preoperative patient anatomical image; and
the image registration step is for driving a radiographic image capturing system to capture an intraoperative patient anatomical image corresponding to the part of the patient's anatomy and disposing a radiographic optical sensing device on the radiographic image capturing system, a body optical sensing device is disposed on the part of the patient's anatomy, the radiographic optical sensing device and the body optical sensing device are both oriented towards an optical tracker to establish the spatial coordinate transformation relationship between the part of the patient's anatomy and the preoperative implant device planning image, the preoperative patient anatomical image is corresponding to the intraoperative patient anatomical image via the spatial coordinate transformation relationship.

3. The no-touch surgical navigation method of claim 1, wherein the instrument checking step comprising:
providing an instrument identifying step, wherein the instrument identifying step is for disposing an instrument optical sensing device on the surgical instrument, and the instrument optical sensing device is oriented towards an optical tracker so as to identify the surgical instrument by the optical tracker.

4. The no-touch surgical navigation method of claim 3, wherein,
the instrument identifying step is for disposing a radio frequency identification tag on the surgical instrument and driving a wireless signal receiver to sense the radio frequency identification tag so as to identify the surgical instrument by the wireless signal receiver.

5. The no-touch surgical navigation method of claim 3, wherein the instrument checking step further comprising:
providing an instrument calibrating step, wherein the instrument calibrating step is for disposing a calibrating optical sensing device on a calibrating device, and then engaging the surgical instrument with the calibrating device, and orienting the surgical instrument and the calibrating device towards the optical tracker, the surgical instrument and the calibrating device are simultaneously identified by the optical tracker to establish a spatial coordinate transformation relationship between a tip of the surgical instrument and the instrument optical sensing device.

6. The no-touch surgical navigation method of claim 5, wherein,
the implant device placement selecting step is for moving the surgical instrument by the user to move the instrument tip mark corresponding to a position of the tip of the surgical instrument in the preoperative implant device planning image, and when the instrument tip mark is moved to a position of the virtual surgical instrument pattern, the preoperative implant device planning image is changed to the skin incision and trajectory guiding picture on the displaying device.

7. The no-touch surgical navigation method of claim 1, wherein the skin incision and trajectory guiding picture comprises:
a transverse plane defined by an area between an x-axis and a z-axis, wherein the virtual surgical instrument pattern and the instrument tip mark are displayed at a first viewing angle in the transverse plane;
a sagittal plane defined by an area between the z-axis and a y-axis, wherein the x-axis, the y-axis and the z-axis define a surgical site coordinate system, and the virtual surgical instrument pattern and the instrument tip mark are displayed at a second viewing angle in the sagittal plane; and
a skin incision aiming image displaying the instrument tip mark and the planned surgical position;
wherein the instrument tip mark of the transverse plane, the instrument tip mark of the sagittal plane and the instrument tip mark of the skin incision aiming image are simultaneously moved with movement of the surgical instrument according to the surgical site coordinate system.

8. The no-touch surgical navigation method of claim 1, wherein,
in the skin incision and trajectory guiding picture, there is a distance between the instrument tip mark and the planned surgical position;
wherein when the distance is greater than a first predetermined distance value, the instrument tip mark is displayed in a first color;

wherein when the distance is smaller than or equal to the first predetermined distance value and greater than a second predetermined distance value, the instrument tip mark is displayed in a second color;

wherein when the distance is smaller than or equal to the second predetermined distance value, the instrument tip mark is displayed in a third color, and the first color, the second color and the third color are different from each other.

9. The no-touch surgical navigation method of claim 1, wherein, the skin incision and trajectory guiding step is for moving the surgical instrument by the user to align the instrument tip mark with the planned surgical position in the skin incision and trajectory guiding picture, and when the instrument tip mark is fully aligned with the planned surgical position for a period of time, the skin incision and trajectory guiding picture is changed to a surgical instrument guiding picture on the displaying device.

10. The no-touch surgical navigation method of claim 9, further comprising:

providing a surgical instrument trajectory guiding step, wherein the surgical instrument trajectory guiding step is for moving a tip and a tail of the surgical instrument close to the planned surgical position according to the surgical instrument guiding picture, and then the tip and the tail of the surgical instrument are simultaneously aligned with the planned surgical position.

11. The no-touch surgical navigation method of claim 10, wherein, the surgical instrument guiding picture displays the instrument tip mark, an instrument tail mark and the planned surgical position, the instrument tail mark is corresponding to the tail of the surgical instrument, the instrument tip mark is spaced from the planned surgical position by a tip distance, and the instrument tail mark is spaced from the planned surgical position by a tail distance;

wherein when the tip distance is greater than a first predetermined distance value, the instrument tip mark is displayed in a first color;

wherein when the tail distance is greater than the first predetermined distance value, the instrument tail mark is displayed in the first color;

wherein when the tip distance is smaller than or equal to the first predetermined distance value and greater than a second predetermined distance value, the instrument tip mark is displayed in a second color;

wherein when the tail distance is smaller than or equal to the first predetermined distance value and greater than a second predetermined distance value, the instrument tail mark is displayed in the second color;

wherein when the tip distance is smaller than or equal to the second predetermined distance value, the instrument tip mark is displayed in a third color;

wherein when the tail distance is smaller than or equal to the second predetermined distance value, the instrument tail mark is displayed in the third color, and the first color, the second color and the third color are different from each other.

12. The no-touch surgical navigation method of claim 1, wherein, the skin incision and trajectory guiding step is for moving the first surgical instrument by the user to align the first instrument tip mark with the planned surgical position in the skin incision and trajectory guiding picture, and when the first instrument tip mark is fully aligned with the planned surgical position for a period of time, the skin incision and trajectory guiding picture is changed to a surgical instrument guiding picture on the displaying device.

13. A no-touch surgical navigation system using the no-touch surgical navigation method of claim 1, comprising:

the surgical instrument moved by the user and connected to an instrument optical sensing device;

the displaying device comprising a screen which displays the preoperative implant device planning image, the skin incision and trajectory guiding picture or a surgical instrument guiding picture;

an optical tracker configured to sense the instrument optical sensing device, wherein the instrument optical sensing device is oriented towards the optical tracker so as to identify the surgical instrument by the optical tracker and obtain a surgical instrument datum corresponding to the surgical instrument; and a processing unit signally connected to the displaying device and the optical tracker, and the processing unit comprising:

a preoperative implant device planning module configured to acquire the preoperative implant device planning image and visualize the preoperative implant device planning image on the screen;

an image registration module signally connected to the preoperative implant device planning module, wherein the image registration module is configured to establish the spatial coordinate transformation relationship between the part of the patient's anatomy and the preoperative implant device planning image, and match the preoperative implant device planning image and the part of the patient's anatomy via the spatial coordinate transformation relationship;

an instrument checking module signally connected to the image registration module and the screen, wherein the instrument checking module is configured to receive the surgical instrument datum and identify a position of the surgical instrument on the screen, and then calibrate the size of the surgical instrument to display the instrument tip mark of the surgical instrument on the screen;

an implant device placement selecting module signally connected to the instrument checking module and the image registration module, wherein the implant device placement selecting module is configured to select a virtual surgical instrument pattern in the preoperative implant device planning image by moving the instrument tip mark of the surgical instrument so as to display the skin incision and trajectory guiding picture on the screen; and a trajectory guiding module signally connected to the instrument checking module and the implant device placement selecting module, wherein the trajectory guiding module is configured to move the instrument tip mark close to a planned surgical position by moving the surgical instrument according to the skin incision and trajectory guiding picture on the screen.

14. The no-touch surgical navigation system of claim 13, further comprising:

a calibrating device detachably connected to the surgical instrument; and a calibrating optical sensing device disposed on the calibrating device oriented towards the optical tracker;

wherein the instrument optical sensing device and the calibrating optical sensing device are oriented towards the optical tracker so as to obtain relative positions of the calibrating device, the surgical instrument and the preoperative implant device planning image by the optical tracker.

15. A no-touch surgical navigation method for guiding a plurality of surgical instruments corresponding to a part of the patient's anatomy, the surgical instruments comprising a first surgical instrument and a second surgical instrument, the no-touch surgical navigation method comprising:
providing a preoperative implant device planning step, wherein the preoperative implant device planning step is for acquiring at least one preoperative implant device planning image and visualizing the preoperative implant device planning image on a displaying device;
providing an image registration step, wherein the image registration step is for establishing a spatial coordinate transformation relationship between the part of the patient's anatomy and the preoperative implant device planning image, and matching the preoperative implant device planning image and the part of the patient's anatomy via the spatial coordinate transformation relationship;
providing a first instrument checking step, wherein the first instrument checking step is for identifying the first surgical instrument, and then calibrating a size of the first surgical instrument to display a first instrument tip mark of the first surgical instrument on the displaying device;
providing an implant device placement selecting step, wherein the implant device placement selecting step is for moving the first surgical instrument by a user, and the first instrument tip mark is synchronously moved with the first surgical instrument to select a virtual second surgical instrument pattern in the preoperative implant device planning image, and then a skin incision and trajectory guiding picture is shown on the displaying device;
providing a skin incision and trajectory guiding step, wherein the skin incision and trajectory guiding step is for moving the first surgical instrument by the user according to the skin incision and trajectory guiding picture so as to move the first instrument tip mark close to a planned surgical position, the planned surgical position is displayed in the skin incision and trajectory guiding picture, and when the first instrument tip mark is aligned with the planned surgical position, the skin incision and trajectory guiding picture is changed to a surgical instrument guiding picture on the displaying device;
providing an instrument replacing step, wherein the instrument replacing step is for replacing the first surgical instrument with the second surgical instrument by the user;
providing a second instrument checking step, wherein the second instrument checking step is for identifying the second surgical instrument, and then calibrating a size of the second surgical instrument to display a second instrument tip mark of the second surgical instrument on the displaying device; and
providing a surgical instrument trajectory guiding step, wherein the surgical instrument trajectory guiding step is for moving the second surgical instrument close to the planned surgical position according to the surgical instrument guiding picture.

16. The no-touch surgical navigation method of claim 15, wherein,
the preoperative implant device planning image includes a preoperative patient anatomical image; and
the image registration step is for driving a radiographic image capturing system to capture an intraoperative patient anatomical image corresponding to the part of the patient's anatomy and disposing a radiographic optical sensing device on the radiographic image capturing system, a body optical sensing device is disposed on the part of the patient's anatomy, the radiographic optical sensing device and the body optical sensing device are both oriented towards an optical tracker to establish the spatial coordinate transformation relationship between the part of the patient's anatomy and the preoperative implant device planning image, the preoperative patient anatomical image is corresponding to the intraoperative patient anatomical image via the spatial coordinate transformation relationship.

17. The no-touch surgical navigation method of claim 15, wherein the first instrument checking step comprising:
providing a first instrument identifying step, wherein the first instrument identifying step is for disposing a first instrument optical sensing device on the first surgical instrument, and the first instrument optical sensing device is oriented towards an optical tracker so as to identify the first surgical instrument by the optical tracker.

18. The no-touch surgical navigation method of claim 17, wherein the first instrument checking step further comprising:
providing a first instrument calibrating step, wherein the first instrument calibrating step is for disposing a calibrating optical sensing device on a calibrating device, and then engaging the first surgical instrument with the calibrating device, and orienting the first surgical instrument and the calibrating device towards the optical tracker, the first surgical instrument and the calibrating device are simultaneously identified by the optical tracker to establish a spatial coordinate transformation relationship between a tip of the first surgical instrument and the first instrument optical sensing device.

19. The no-touch surgical navigation method of claim 18, wherein,
the implant device placement selecting step is for moving the first surgical instrument by the user to move the first instrument tip mark corresponding to a position of the tip of the first surgical instrument in the preoperative implant device planning image, and when the first instrument tip mark is moved to a position of the virtual second surgical instrument pattern, the preoperative implant device planning image is changed to the skin incision and trajectory guiding picture on the displaying device.

20. The no-touch surgical navigation method of claim 15, wherein the skin incision and trajectory guiding picture comprises:
a transverse plane defined by an area between an x-axis and a z-axis, wherein the virtual second surgical instrument pattern and the first instrument tip mark are displayed at a first viewing angle in the transverse plane;
a sagittal plane defined by an area between the z-axis and a y-axis, wherein the x-axis, the y-axis and the z-axis define a surgical site coordinate system, and the virtual second surgical instrument pattern and the first instrument tip mark are displayed at a second viewing angle in the sagittal plane; and a skin incision aiming image displaying the first instrument tip mark and the planned surgical position;

wherein the first instrument tip mark of the transverse plane, the first instrument tip mark of the sagittal plane and the first instrument tip mark of the skin incision aiming image are simultaneously moved with movement of the first surgical instrument according to the surgical site coordinate system.

21. The no-touch surgical navigation method of claim 15, wherein, in the skin incision and trajectory guiding picture, there is a distance between the first instrument tip mark and the planned surgical position;

wherein when the distance is greater than a first predetermined distance value, the first instrument tip mark is displayed in a first color;

wherein when the distance is smaller than or equal to the first predetermined distance value and greater than a second predetermined distance value, the first instrument tip mark is displayed in a second color;

wherein when the distance is smaller than or equal to the second predetermined distance value, the first instrument tip mark is displayed in a third color, and the first color, the second color and the third color are different from each other.

22. The no-touch surgical navigation method of claim 15, wherein the second instrument checking step comprising:

providing a second instrument identifying step, wherein the second instrument identifying step is for disposing a second instrument optical sensing device on the second surgical instrument, and the second instrument optical sensing device is oriented towards an optical tracker so as to identify the second surgical instrument by the optical tracker.

23. The no-touch surgical navigation method of claim 22, wherein, the second instrument identifying step is for disposing a radio frequency identification tag on the second surgical instrument and driving a wireless signal receiver to sense the radio frequency identification tag so as to identify the second surgical instrument by the wireless signal receiver.

24. The no-touch surgical navigation method of claim 22, wherein the second instrument checking step further comprising:

providing a second instrument calibrating step, wherein the second instrument calibrating step is for disposing a calibrating optical sensing device on a calibrating device, and then engaging the second surgical instrument with the calibrating device, and orienting the second surgical instrument and the calibrating device towards the optical tracker, the second surgical instrument and the calibrating device are simultaneously identified by the optical tracker to establish a spatial coordinate transformation relationship between a tip of the second surgical instrument and the second instrument optical sensing device.

25. The no-touch surgical navigation method of claim 15, wherein, the surgical instrument guiding picture displays the second instrument tip mark, a second instrument tail mark and the planned surgical position, the second instrument tail mark is corresponding to a tail of the second surgical instrument, the second instrument tip mark is spaced from the planned surgical position by a tip distance, and the second instrument tail mark is spaced from the planned surgical position by a tail distance;

wherein when the tip distance is greater than a first predetermined distance value, the second instrument tip mark is displayed in a first color;

wherein when the tail distance is greater than the first predetermined distance value, the second instrument tail mark is displayed in the first color;

wherein when the tip distance is smaller than or equal to the first predetermined distance value and greater than a second predetermined distance value, the second instrument tip mark is displayed in a second color;

wherein when the tail distance is smaller than or equal to the first predetermined distance value and greater than the second predetermined distance value, the second instrument tail mark is displayed in the second color;

wherein when the tip distance is smaller than or equal to the second predetermined distance value, the second instrument tip mark is displayed in a third color;

wherein when the tail distance is smaller than or equal to the second predetermined distance value, the second instrument tail mark is displayed in the third color, and the first color, the second color and the third color are different from each other.

26. The no-touch surgical navigation method of claim 15, wherein, the surgical instrument trajectory guiding step is for moving the second surgical instrument to fully align the second instrument tip mark and a second instrument tail mark with the planned surgical position according to the surgical instrument guiding picture, the second instrument tip mark is corresponding to a tip of the second surgical instrument, and the second instrument tail mark is corresponding to a tail of the second surgical instrument.

* * * * *